US012079992B1

(12) United States Patent
Lazar et al.

(10) Patent No.: US 12,079,992 B1
(45) Date of Patent: Sep. 3, 2024

(54) UTILIZING MACHINE LEARNING AND DIGITAL EMBEDDING PROCESSES TO GENERATE DIGITAL MAPS OF BIOLOGY AND USER INTERFACES FOR EVALUATING MAP EFFICACY

(71) Applicant: Recursion Pharmaceuticals, Inc., Salt Lake City, UT (US)

(72) Inventors: Nathan Henry Lazar, Salt Lake City, UT (US); Conor Austin Forsman Tillinghast, Salt Lake City, UT (US); James Douglas Jensen, Farmington, UT (US); James Benjamin Taylor, Midlothian, VA (US); Berton Allen Earnshaw, Cedar Hills, UT (US); Marta Marie Fay, Salt Lake City, UT (US); Renat Nailevich Khaliullin, Salt Lake City, UT (US); Jacob Carter Cooper, Sandy, UT (US); Imran Saeedul Haque, Salt Lake City, UT (US); Seyhmus Guler, Salt Lake City, UT (US); Kyle Rollins Hansen, Kaysville, UT (US); Safiye Celik, Sudbury, MA (US)

(73) Assignee: Recursion Pharmaceuticals, Inc., Salt Lake City, UT (US)

( * ) Notice: Subject to any disclaimer, the term of this patent is extended or adjusted under 35 U.S.C. 154(b) by 0 days.

(21) Appl. No.: 18/393,041

(22) Filed: Dec. 21, 2023

Related U.S. Application Data

(60) Provisional application No. 63/582,702, filed on Sep. 14, 2023.

(51) Int. Cl.
*G06K 9/00* (2022.01)
*G06T 7/00* (2017.01)
(Continued)

(52) U.S. Cl.
CPC .......... *G06T 7/0012* (2013.01); *G06V 10/761* (2022.01); *G06V 10/95* (2022.01);
(Continued)

(58) Field of Classification Search
None
See application file for complete search history.

(56) References Cited

U.S. PATENT DOCUMENTS

| 10,146,914 B1 | 12/2018 | Victors et al. |
| 10,769,501 B1 | 9/2020 | Ando et al. |

(Continued)

OTHER PUBLICATIONS

Ando et al., "Improving phenotype measurements in high-content imaging screens" (Year: 2017).*

(Continued)

*Primary Examiner* — SJ Park
(74) *Attorney, Agent, or Firm* — Keller Preece PLLC

(57) ABSTRACT

The present disclosure relates to systems, non-transitory computer-readable media, and methods for utilizing machine learning and digital embedding processes to generate digital maps of biology and user interfaces for evaluating map efficacy. In particular, in one or more embodiments, the disclosed systems receive perturbation data for a plurality of perturbation experiment units corresponding to a plurality of perturbation classes. Further, the systems generate, utilizing a machine learning model, a plurality of perturbation experiment unit embeddings from the perturbation data. Additionally, the systems align, utilizing an alignment model, the plurality of perturbation experiment unit embeddings to generate aligned perturbation unit embeddings. Moreover, the systems aggregate the aligned perturbation unit embeddings to generate aggregated embeddings. Furthermore, the systems generate perturbation comparisons utilizing the perturbation-level embeddings.

20 Claims, 22 Drawing Sheets

(51) Int. Cl.
  *G06V 10/74* (2022.01)
  *G06V 10/94* (2022.01)
  *G06V 20/69* (2022.01)
  *G16B 40/00* (2019.01)

(52) U.S. Cl.
  CPC ........... *G06V 20/698* (2022.01); *G16B 40/00* (2019.02); *G06T 2200/24* (2013.01); *G06T 2207/20081* (2013.01); *G06T 2207/30072* (2013.01)

(56) References Cited

U.S. PATENT DOCUMENTS

| | | |
|---|---|---|
| 2019/0114390 A1 | 4/2019 | Donner et al. |
| 2021/0133976 A1 | 5/2021 | Carmi |
| 2021/0366577 A1 | 11/2021 | Koller et al. |
| 2022/0180975 A1 | 6/2022 | Regev et al. |

OTHER PUBLICATIONS

Ando (Year: 2017).*
Akshay Agrawal, Alnur Ali, Stephen Boyd, et al. Minimum-distortion embedding. Foundations and Trends® in Machine Learning, 14(3):211-378, 2021.
Arthur Liberzon, Chet Birger, Helga Thorvaldsdóttir, Mahmoud Ghandi, Jill P Mesirov, and Pablo Tamayo. The molecular signatures database hallmark gene set collection. Cell systems, 1(6):417-425, 2015.
Atray Dixit, Oren Parnas, Biyu Li, Jenny Chen, Charles P Fulco, Livnat Jerby-Arnon, Nemanja D Marjanovic, Danielle Dionne, Tyler Burks, Raktima Raychowdhury, et al. Perturb-seq: dissecting molecular circuits with scalable single-cell rna profiling of pooled genetic screens. cell, 167(7):1853-1866, 2016.
Aurora S Blucher, Safiye Celik, James D Jensen, James Taylor, Michael F Cuccarese, Jacob C Cooper, Jacob M Rinaldi, Carl Brooks, Michael A Statnick, Marta Fay, Nathan Lazar, Berton Earnshaw, and Imran S Haque. Poster: Mapping biology with a unified representation space for genomic and chemical perturbations to enable accelerated drug discovery. In Learning Meaningful Representation of Life Workshop at NeurIPS, 2021.
Gabor J Szekely. Potential and kinetic energy in statistics. Lecture Notes, Budapest Institute, 1989.
Gökcen Eraslan, Lukas M Simon, Maria Mircea, Nikola S Mueller, and Fabian J Theis. Singlecell rna-seq denoising using a deep count autoencoder. Nature communications, 10(1):1-14, 2019.
John W Tukey. Mathematics and the picturing of data. In Proceedings of the International Congress of Mathematicians, Vancouver, 1975, vol. 2, pp. 523-531, 1975.
Joseph M Replogle, Reuben A Saunders, Angela N Pogson, Jeffrey A Hussmann, Alexander Lenail, Alina Guna, Lauren Mascibroda, Eric J Wagner, Karen Adelman, Gila Lithwick-Yanai, et al. Mapping information-rich genotype-phenotype landscapes with genome-scale perturb-seq. Cell, 2022.
Kevin Drew, John B Wallingford, and Edward M Marcotte. hu.map 2.0: integration of over 15,000 proteomic experiments builds a global compendium of human multiprotein assemblies. Mol Syst Biol, 17(5):e10016, 2021.
Kihyuk Sohn, Honglak Lee, and Xinchen Yan. Learning structured output representation using deep conditional generative models. Advances in neural information processing systems, 28, 2015.
Krzysztof Polanski, Matthew D Young, Zhichao Miao, Kerstin B Meyer, Sarah A Teichmann, and Jong-Eun Park. Bbknn: fast batch alignment of single cell transcriptomes. Bioinformatics, 36(3):964-965, 2020.
Laleh Haghverdi, Aaron TL Lun, Michael D Morgan, and John C Marioni. Batch effects in single-cell rna-sequencing data are corrected by matching mutual nearest neighbors. Nature biotechnology, 36(5):421-427, 2018.
Leland McInnes, John Healy, and James Melville. Umap: Uniform manifold approximation and projection for dimension reduction. arXiv preprint arXiv:1802.03426, 2018.
Luana Licata, Prisca Lo Surdo, Marta Iannuccelli, Alessandro Palma, Elisa Micarelli, Livia Perfetto, Daniele Peluso, Alberto Calderone, Luisa Castagnoli, and Gianni Cesareni. Signor 2.0, the signaling network open resource 2.0: 2019 update. Nucleic acids research, 48(D1): D504-D510, 2020.
Madalina Giurgiu, Julian Reinhard, Barbara Brauner, Irmtraud Dunger-Kaltenbach, Gisela Fobo, Goar Frishman, Corinna Montrone, and Andreas Ruepp. Corum: the comprehensive resource of mammalian protein complexes—2019. Nucleic acids research, 47(D1):D559-D563, 2019.
Marc Gillespie, Bijay Jassal, Ralf Stephan, Marija Milacic, Karen Rothfels, Andrea Senff-Ribeiro, Johannes Griss, Cristoffer Sevilla, Lisa Matthews, Chuqiao Gong, et al. The reactome pathway knowledgebase 2022. Nucleic acids research, 50(D1):D687-D692, 2022.
Maria L Rizzo and Gábor J Székely. Energy distance. wiley interdisciplinary reviews: Computational statistics, 8(1):27-38, 2016.
Mark-Anthony Bray, Shantanu Singh, Han Han, Chadwick T Davis, Blake Borgeson, Cathy Hartland, Maria Kost-Alimova, Sigrun M Gustafsdottir, Christopher C Gibson, and Anne E Carpenter. Cell painting, a high-content image-based assay for morphological profiling using multiplexed fluorescent dyes. Nature protocols, 11(9):1757-1774, 2016.
Michael F Cuccarese, Berton A Earnshaw, Katie Heiser, Ben Fogelson, Chadwick T Davis, Peter F McLean, Hannah B Gordon, Kathleen-Rose Skelly, Fiona L Weathersby, Vlad Rodic, Ian K Quigley, Elissa D Pastuzyn, Brandon M Mendivil, Nathan H Lazar, Carl A Brooks, Joseph Carpenter, Brandon L Probst, Pamela Jacobson, Seth W Glazier, Jes Ford, James D Jensen, Nicholas D Campbell, Michael A Statnick, Adeline S Low, Kirk R Thomas, Anne ECarpenter, Sharath S Hegde, Ronald W Alfa, Mason L Victors, Imran S Haque, Yolanda T Chong, and Christopher C Gibson. Functional immune mapping with deep-learning enabled phenomics applied to immunomodulatory and covid-19 drug discovery. bioRxiv, 2020. doi: 10.1101/2020.08.02.233064.
Nathan Lazar, et al. High-Resolution Genome-wide Mapping of Chromosome-arm-scale Truncations Induced by CRISPR-Cas9 Editing published in bioRxiv on Apr. 15, 2023.
Romain Lopez, Jeffrey Regier, Michael B Cole, Michael I Jordan, and Nir Yosef. Deep generative modeling for single-cell transcriptomics. Nature methods, 15(12):1053-1058, 2018.
Sivanandan et al. "A Pooled Cell Painting CRISPR Screening Platform Enables de novo Inference of Gene Function by Self-supervised Deep Learning" https://www.biorxiv.org/contenU10.1101/2023.08.13.553051v3.abstract, bioRxiv2023.08.13.553051; https://doi.org/10.1101/2023.08.13.553051; pp. 1-49; Aug. 27, 2023 (Year: 2023).
U.S. Appl. No. 18/392,989, filed Mar. 1, 2024, Office Action.
U.S. Appl. No. 18/392,989, Mail Date Apr. 29, 2024, Notice of Allowance.

* cited by examiner

| Consistency | Transcriptomic data | | Phenomic data | |
| --- | --- | --- | --- | --- |
| | PCA | scVI | Centerscale | TVN |
| Consistency | 52% | 61% | -1.9% | +100% |
| Distance | 51% | 53% | +5.8% | +109.1% |

*Fig. 7*

|              | Centerscale | TVN      |
|--------------|-------------|----------|
| Consistency  | +583%       | +1292.7% |
| Distance     | +493.3%     | +1072.3% |

Fig. 8

|  | All genes | | Genes w/ transcriptoprint | |
|---|---|---|---|---|
|  | PCA | scVI | PCA | scVI |
| Reactome pairs | 18.6% | 19.8% | 24.4% | 25.4% |
| SIGNOR pairs | 12.4% | 12.9% | 13.2% | 15.2% |
| CORUM clusters | 30.2% | 33% | 38.9% | 40.9% |
| Reactome clusters | 16.1% | 16.9% | 18.6% | 19.6% |
| SIGNOR clusters | 11.4% | 13.3% | 11.9% | 13% |

Fig. 10

|  | All genes | | Genes w/ transcriptoprint | |
|---|---|---|---|---|
|  | PCA | scVI | PCA | scVI |
| Reactome pairs | 10,379 | 10,379 | 3812 | 5120 |
| SIGNOR pairs | 5909 | 5909 | 2014 | 2751 |
| CORUM clusters | 33,175 | 33,175 | 19,034 | 24,122 |
| Reactome clusters | 2,609,505 | 2,609,505 | 896,961 | 1,166,333 |
| SIGNOR clusters | 5981 | 5981 | 1766 | 2413 |

*Fig. 11*

|  | All genes | | Genes w/ phenoprint | |
|---|---|---|---|---|
|  | Centerscale | TVN | Centerscale | TVN |
| Reactome pairs | +14.5% | +82.1% | +6.5% | +15% |
| SIGNOR pairs | -4.9% | +55.1% | -3.5% | +26.3% |
| CORUM clusters | +18.2% | +107.1% | +10.2% | +18.8% |
| Reactome clusters | +6.5% | +62.9% | +1% | +8.7% |
| SIGNOR clusters | -11.5% | +52.9% | +14.1% | +142.7% |

*Fig. 14*

|  | All genes | | Genes w/ phenoprint | |
| --- | --- | --- | --- | --- |
|  | Centerscale | TVN | Centerscale | TVN |
| Reactome pairs | 18,486 | 18,486 | 3273 | 7209 |
| SIGNOR pairs | 10,484 | 10,484 | 1570 | 3858 |
| CORUM clusters | 27,890 | 27,890 | 15,227 | 23,050 |
| Reactome clusters | 5,022,964 | 5,022,964 | 592,737 | 1,528,163 |
| SIGNOR clusters | 11,312 | 11,312 | 1537 | 3610 |

Fig. 15

UTILIZING MACHINE LEARNING AND DIGITAL EMBEDDING PROCESSES TO GENERATE DIGITAL MAPS OF BIOLOGY AND USER INTERFACES FOR EVALUATING MAP EFFICACY

CROSS REFERENCE TO RELATED APPLICATIONS

This application claims the benefit of and priority to U.S. Provisional Application No. 63/582,702, filed Sep. 14, 2023. The aforementioned application is hereby incorporated by reference in its entirety.

BACKGROUND

Recent years have seen significant developments in hardware and software platforms for utilizing machine learning tools to analyze underlying datasets and generate machine learning predictions. For example, conventional systems can analyze a variety of data structures corresponding to biological assays to generate one or more biological treatment predictions. Despite recent advancements, conventional systems continue to experience a variety of technical problems, including accuracy, flexibility, and efficiency of implementing computing devices.

SUMMARY

Embodiments of the present disclosure provide benefits and/or solve one or more of the foregoing or other problems in the art with systems, non-transitory computer-readable media, and methods for utilizing machine learning and digital embedding processes to generate digital maps of biology and user interfaces for evaluating map efficacy. In particular, the disclosed systems can embed perturbation experiment unit measurements representing cell perturbations into a low dimensional space via a machine learning model. Moreover, in one or more embodiments, the disclosed systems apply various filtering, aligning, and aggregation models to the perturbation experiment unit embeddings to generate a perturbation-level embedding for each perturbation class. Additionally, the disclosed systems can relate the perturbation-level embeddings to one another to generate, for display at a client device, a digital map of biology including one or more perturbation comparisons. Furthermore, in some implementations, the disclosed systems receive perturbation data and determines benchmark measures, for display via a client device, of the perturbation data.

Additional features and advantages of one or more embodiments of the present disclosure are outlined in the description which follows, and in part can be determined from the description, or may be learned by the practice of such example embodiments.

BRIEF DESCRIPTION OF THE DRAWINGS

The detailed description provides one or more embodiments with additional specificity and detail through the use of the accompanying drawings, as briefly described below.

FIG. 7 illustrates perturbation print rates based on the univariate benchmark measure metrics of consistency and distance in accordance with one or more embodiments.

FIG. 8 illustrates phenoprint rates for a phenomic map in accordance with one or more embodiments.

FIG. 10 illustrates multivariate metrics/benchmarks in accordance with one or more embodiments.

FIG. 11 illustrates relationship counts for multivariate benchmarks on phenomic data in accordance with one or more embodiments.

FIG. 14 illustrates multivariate metrics/benchmarks in phenomic data in accordance with one or more embodiments.

FIG. 15 illustrates known relationship counts for multivariate benchmarks on phenomic data in accordance with one or more embodiments.

DETAILED DESCRIPTION

Figure 1:
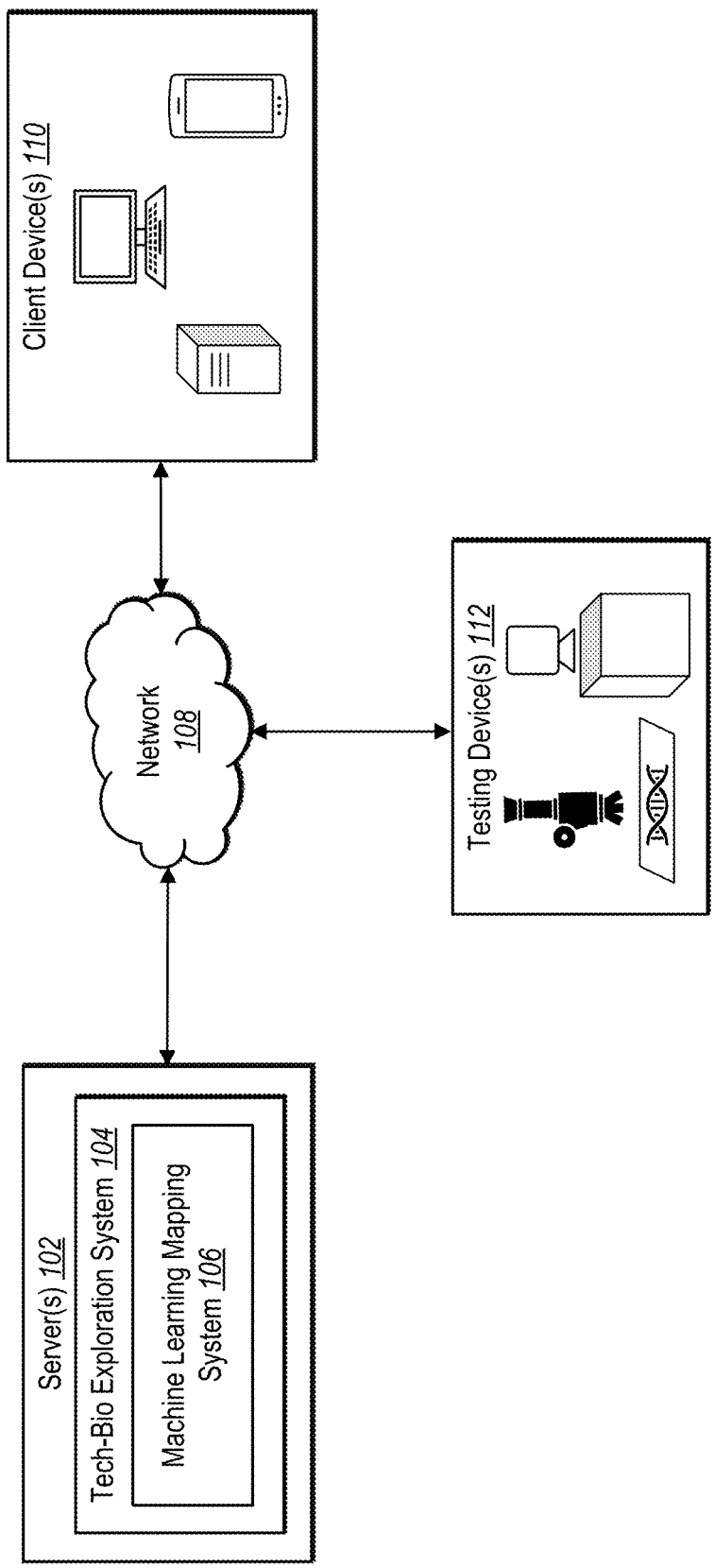
FIG. 1 illustrates a schematic diagram of a system environment in which a machine learning mapping system can operate in accordance with one or more embodiments.

This disclosure describes one or more embodiments of a machine learning mapping system that utilizes machine learning and digital embedding processes to generate digital maps of biology and user interfaces for evaluating map efficacy. In particular, in some embodiments, the machine learning mapping system embeds perturbation experiment unit measurements representing cell perturbations into a low dimensional space via a machine learning model. Moreover, the machine learning mapping system can apply various filtering, aligning, and aggregation models to the perturbation experiment unit embeddings to generate a perturbation-level embedding for each perturbation class. Additionally, the machine learning mapping system can relate the perturbation-level embeddings to one another to generate, for display at a client device, a digital map of biology including one or more perturbation comparisons. Furthermore, in some implementations, the machine learning mapping system receives perturbation data and determines benchmark measures, for display via a client device, of the perturbation data.

As just mentioned, the machine learning mapping system can embed perturbation experiment unit measurements representing cell perturbations into a low dimensional space via a machine learning model. For example, the machine learning mapping system can receive perturbation data from a variety of perturbation experiments. Indeed, the perturbation experiments can include measurements from a wide variety of biological treatments. Moreover, in one or more embodiments, each measurement represents a perturbation experiment unit. The machine learning mapping system can utilize a machine learning model (e.g., a foundation model) to embed the perturbation experiment unit measurements.

Further, as mentioned above, the machine learning mapping system can apply various filtering, aligning, and aggregating models to the perturbation experiment unit embeddings to generate a perturbation-level embedding for each perturbation class. For instance, the machine learning mapping system can filter outlying perturbation experiment unit embeddings according to one or more quality criterion using a filtration model. Additionally, the machine learning mapping system can align, utilizing an aligning model, the filtered embeddings across many perturbation experiments to accurately relate the filtered embeddings of each perturbation class to one another, thereby eliminating inaccuracies, such as batch effects, from various sources. Moreover, the machine learning mapping system can utilize an aggregating model to aggregate the aligned embeddings to generate a single perturbation-level embedding for each perturbation class.

Moreover, as noted above, the machine learning mapping system can relate the perturbation-level embeddings to one another to generate, for display at a client device, a digital map of biology including one or more perturbation comparisons. For example, in some implementations, the machine learning mapping system determines similarity measures between the perturbation-level embeddings. Further, the machine learning mapping system can provide the similarity measures to various computing devices across computer networks for dynamic display of the similarity measures.

Furthermore, as mentioned previously, the machine learning mapping system can receive perturbation data and determine benchmark measures of the perturbation data. For instance, the machine learning mapping system can receive perturbation data including perturbation experiment unit embeddings and/or similarity measures between perturbation-level embeddings for perturbation classes. Moreover, in some embodiments, the machine learning mapping system determines a benchmark measure for the perturbation data utilizing a benchmark model. For example, the machine learning mapping system can determine a univariate benchmark measure for the perturbation experiment unit embeddings assessing perturbation quality. In additional example, the machine learning mapping system can determine a multivariate benchmark measure for the similarity measures between the perturbation-level embeddings assessing recovery of known, and identification of new, biological relationships. Moreover, in one or more implementations, the machine learning mapping system can provide these various benchmarks for dynamic evaluation of biological maps to various computing devices across computer networks.

As mentioned above, although conventional systems can analyze a variety of data structures corresponding to biological assays to generate one or more biological treatment predictions, such systems have a number of problems in relation to accuracy, efficiency, and flexibility of operation. For instance, conventional systems inaccurately relate perturbation data across experiments. Specifically, conventional systems inaccurately portray interrelationships between underlying biological data. For instance, conventional systems cannot accurately identify biological relationships between perturbations when the underlying measurements arise from different experiments. Indeed, conventional systems inaccurately relate signals detected in multiple experiments resulting in misidentification of biological relationships due to experiment specific variation in detected signals. Moreover, conventional systems lack the ability to accurately benchmark biological signals detected during perturbation experiments and biological relationship measures resulting therefrom.

Furthermore, conventional systems demonstrate operational inflexibility by failing to implement a variety of tools for relating biological data, in addition to their inaccuracies. For instance, conventional systems do not use tools such as machine learning models or benchmarking of biological maps. Specifically, conventional systems rely on rigid query approaches without transforming the data using machine learning models or without employing various machine learning models to generate digital maps. Moreover, conventional systems do not flexibly analyze biological mapping systems with a variety of different benchmarks.

In addition to their inaccuracies and inflexibility, conventional systems inefficiently collect and compare biological relationship data. More specifically, conventional systems cannot collect high-volume datasets spanning multiple experiments for comparison without a high number of inputs and user interfaces. Further, conventional systems utilize a brute-force approach requiring many additional user interactions, processes, and interfaces to discover potential interrelationships and/or to benchmark these interrelationships even after the collection of the data.

As suggested by the foregoing, the machine learning mapping system provides a variety of technical advantages relative to conventional systems. For example, the machine learning mapping system can improve accuracy of implementing computing devices by generating improved machine learning representations and digital maps portraying interrelationships between underlying biological data. In particular, the machine learning mapping system can generate improved embeddings for comparing and identifying interrelationships between genes, compounds, proteins, or other biological features. Moreover, the machine learning mapping system can also generate more accurate metrics or benchmarks for biological maps and provide these benchmarks for display via user interfaces to improve analysis and utilization of underlying processes.

In addition, the machine learning mapping system can also improve flexibility by utilizing various machine learning models to generate digital maps reflecting a variety of different underlying biological processes or interactions.

Furthermore, the machine learning mapping system can utilize a variety of different benchmarks to flexibly analyze the efficacy of resulting digital maps.

Furthermore, the machine learning mapping system can improve efficiency of implementing computing systems. As mentioned above, the machine learning mapping system can generate and combine high-volume datasets representing millions of assays into efficient machine learning representations for efficient utilization and analysis. Indeed, by improving machine learning representations, resulting digital maps, and corresponding benchmarks, the machine learning mapping system can save significant expenditures in time and computing power in identifying interrelationships between genes, compounds, proteins, doses, or treatments. Thus, the machine learning mapping system can significantly shortcut analysis and time required to identify and explore various tech-bio spaces, streamlining and improving the overall system environment.

Additional detail regarding a machine learning mapping system 106 will now be provided with reference to the figures. In particular, FIG. 1 illustrates a schematic diagram of a system environment in which the machine learning mapping system 106 can operate in accordance with one or more embodiments.

As shown in FIG. 1, the environment includes server(s) 102 (which includes a tech-bio exploration system 104 and the machine learning mapping system 106), a network 108, client device(s) 110, and testing device(s) 112. As further illustrated in FIG. 1, the various computing devices within the environment can communicate via the network 108. Although FIG. 1 illustrates the machine learning mapping system 106 being implemented by a particular component and/or device within the environment, the machine learning mapping system 106 can be implemented, in whole or in part, by other computing devices and/or components in the environment (e.g., the client device(s) 110). Additional description regarding the illustrated computing devices is provided with respect to FIG. 19 below.

As shown in FIG. 1, the server(s) 102 can include the tech-bio exploration system 104. In some embodiments, the tech-bio exploration system 104 can determine, store, generate, analyze and/or display tech-bio information including maps of biology, biology experiments from various sources, and/or machine learning tech-bio predictions. For instance, the tech-bio exploration system 104 can analyze data signals corresponding to various treatments or interventions (e.g., compounds or biologics) and the corresponding relationships in genetics, proteomics, phenomics (i.e., cellular phenotypes), and invivomics (e.g., expressions or results within a living animal). In one or more embodiments, the server(s) 102 comprises a data server. In some implementations, the server(s) 102 comprises a communication server or a web-hosting server.

Further, the tech-bio exploration system 104 can generate and access experimental results corresponding to gene sequences, protein shapes/folding, protein/compound interactions, phenotypes resulting from various interventions or perturbations (e.g., gene knockout sequences or compound treatments), and/or in vivo experimentation on various treatments in living animals. By analyzing these signals (e.g., utilizing various machine learning models), the tech-bio exploration system 104 can generate or determine a variety of predictions and inter-relationships for improving treatments/interventions.

To illustrate, the tech-bio exploration system 104 can generate maps of biology indicating biological inter-relationships or similarities between these various input signals to discover potential new treatments. For example, the tech-bio exploration system 104 can utilize machine learning and/or maps of biology to identify a similarity between a first gene associated with disease treatment and a second gene previously unassociated with the disease based on a similarity in resulting phenotypes from gene knockout experiments. The tech-bio exploration system 104 can then identify new treatments based on the gene similarity (e.g., by targeting compounds the impact the second gene). Similarly, the tech-bio exploration system 104 can analyze signals from a variety of sources (e.g., protein interactions, or in vivo experiments) to predict efficacious treatments based on various levels of biological data.

The tech-bio exploration system 104 can generate GUIs comprising dynamic user interface elements to convey tech-bio information and receive user input for intelligently exploring tech-bio information. Indeed, as mentioned above, the tech-bio exploration system 104 can generate GUIs displaying different maps of biology that intuitively and efficiently express complex interactions between different biological systems for identifying improved treatment solutions. Furthermore, the tech-bio exploration system 104 can also electronically communicate tech-bio information between various computing devices.

As shown in FIG. 1, the tech-bio exploration system 104 can include a system that facilitates various models or algorithms for generating maps of biology (e.g., maps or visualizations illustrating similarities or relationships between genes, proteins, diseases, compounds, and/or treatments) and discovering new treatment options over one or more networks. For example, the tech-bio exploration system 104 collects, manages, and transmits data across a variety of different entities, accounts, and devices. In some cases, the tech-bio exploration system 104 is a network system that facilitates access to (and analysis of) tech-bio information within a centralized operating system. Indeed, the tech-bio exploration system 104 can link data from different network-based research institutions to generate and analyze maps of biology.

As shown in FIG. 1, the tech-bio exploration system 104 can include a system that comprises the machine learning mapping system 106 that generates, stores, manages, transmits, and analyzes cell and subject perturbation datasets. For example, the machine learning mapping system 106 can generate perturbation experiment unit embeddings utilizing a machine learning model and synthesize the embeddings according to various filtration, alignment, and aggregation models. Further, the machine learning mapping system 106 can identify similarity measures between aggregated perturbation embeddings (e.g., perturbation-level embeddings) of a perturbation embedding model and determine a benchmark measure for the perturbation embedding model. For example, the machine learning mapping system 106 can generate a univariate benchmark measure for the perturbation experiment unit embeddings of the perturbation embedding model and/or a multivariate benchmark measure for the identified similarity measures for display.

As used herein, the term "machine learning model" includes a computer algorithm or a collection of computer algorithms that can be trained and/or tuned based on inputs to approximate unknown functions. For example, a machine learning model can include a computer algorithm with branches, weights, or parameters that changed based on training data to improve for a particular task. Thus, a machine learning model can utilize one or more learning techniques (e.g., supervised or unsupervised learning) to improve in accuracy and/or effectiveness. Example machine learning models include various types of decision trees, support vector machines, Bayesian networks, random forest models, or neural networks (e.g., deep neural networks, generative adversarial neural networks, convolutional neural networks, recurrent neural networks, or diffusion neural networks). Similarly, the term "machine learning data" refers to information, data, or files generated or utilized by a machine learning model. Machine learning data can include training data, machine learning parameters, or embeddings/predictions generated by a machine learning model.

As also illustrated in FIG. 1, the environment includes the client device(s) 110. For example, the client device(s) 110 may include, but is not limited to, a mobile device (e.g., smartphone, tablet) or other type of computing device, including those explained below with reference to FIG. 19. Additionally, the client device(s) 110 can include a computing device associated with (and/or operated by) user accounts for the tech-bio exploration system 104. Moreover, the environment can include various numbers of client devices that communicate and/or interact with the tech-bio exploration system 104 and/or the machine learning mapping system 106.

Furthermore, in one or more implementations, the client device(s) 110 includes a client application. The client application can include instructions that (upon execution) cause the client device(s) 110 to perform various actions. For example, a user of a user account can interact with the client application on the client device(s) 110 to access tech-bio information, initiate a request for a benchmark measure and/or generate GUIs comprising similarity measures, benchmark measures, or other machine learning dataset and/or machine learning predictions/results.

As further shown in FIG. 1, the environment includes the network 108. As mentioned above, the network 108 can enable communication between components of the environment. In one or more embodiments, the network 108 may include a suitable network and may communicate using a various number of communication platforms and technologies suitable for transmitting data and/or communication signals, examples of which are described with reference to FIG. 19. Furthermore, although FIG. 1 illustrates computing devices communicating via the network 108, the various components of the environment can communicate and/or interact via other methods (e.g., communicate directly).

As mentioned previously, in one or more implementations, the machine learning mapping system 106 generates and accesses machine learning objects, such as results from biological assays, in vivo trials, results from perturbation embedding models, etc. As shown, in FIG. 1, the machine learning mapping system 106 can communicate with testing device(s) 112 to obtain and then store this information. For example, the tech-bio exploration system 104 can interact with the testing device(s) 112 that include intelligent robotic devices and camera devices for generating and capturing digital images of cellular phenotypes resulting from different perturbations (e.g., genetic knockouts or compound treatments of stem cells). Similarly, the testing device(s) can include camera devices and/or other sensors (e.g., heat or motion sensors) capturing real-time information from animals as part of in vivo experimentation. The tech-bio exploration system 104 can also interact with a variety of other testing device(s) such as devices for determining, generating, or extracting gene sequences or protein information.

Figure 2:
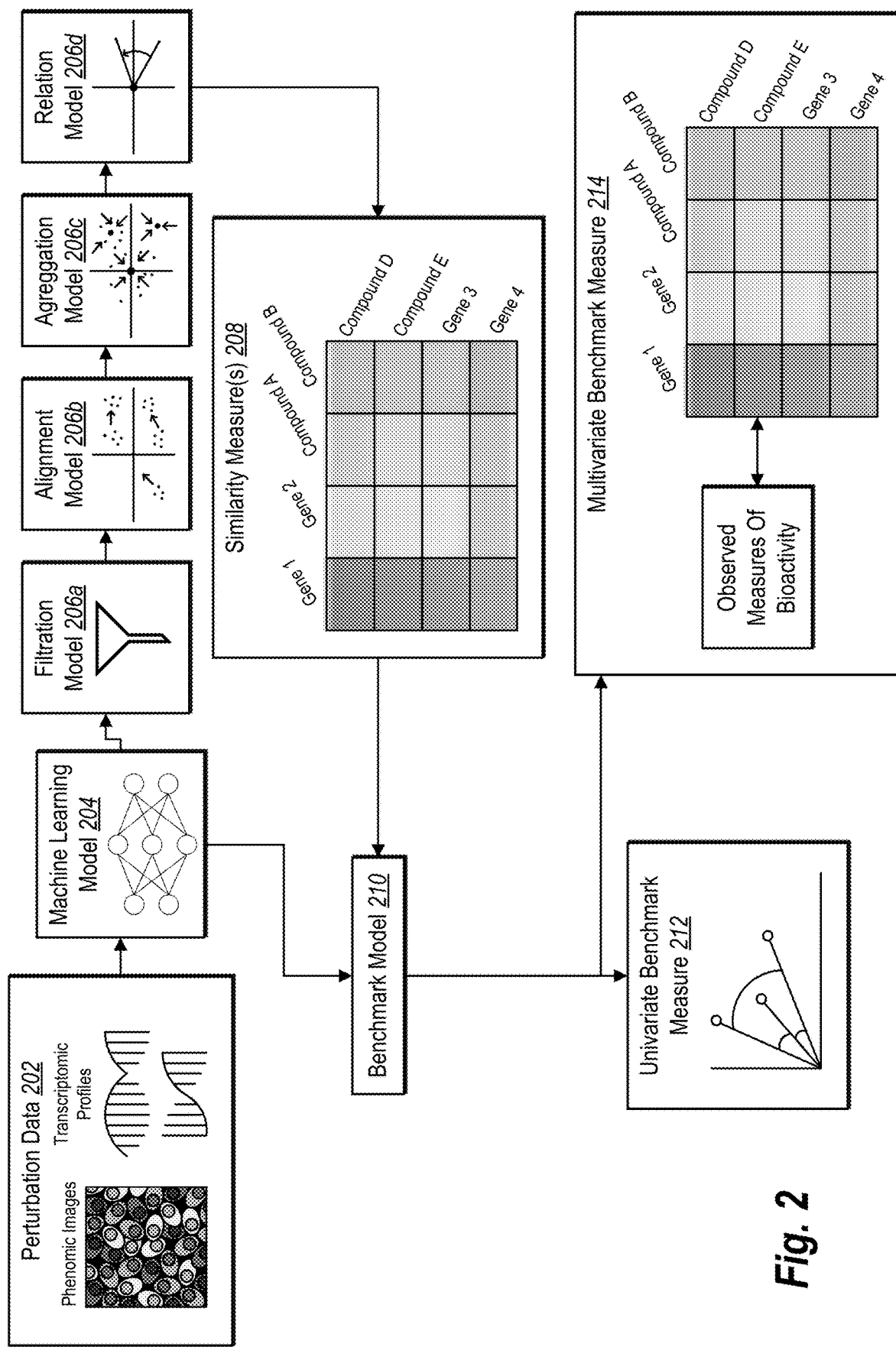
FIG. 2 illustrates generating similarity measures and evaluating perturbation data by embedding and synthesizing the perturbation data in accordance with one or more embodiments.

As mentioned above, the machine learning mapping system 106 can embed perturbation data via a machine learning model and filter, align, and aggregate the embeddings to generate digital maps of biology and user interfaces for evaluating map efficacy. For example, FIG. 2 illustrates generating similarity measures and evaluating perturbation data by embedding and synthesizing the perturbation data in accordance with one or more embodiments. Specifically, the machine learning mapping system 106 receives perturbation data and embeds the data utilizing a machine learning model 204. Further, the machine learning mapping system 106 applies various models such as a filtration model 206a, an alignment model 206b, an aggregation model 206c, and a relation model 206d to the perturbation experiment unit embeddings. Specifically, 106 generates a similarity measure 208 with the relation model 206d. Moreover, the machine learning mapping system 106 uses a benchmark model 210 to determine a univariate benchmark measure 212 and/or a multivariate benchmark measure 214 for the perturbation data 202.

Figure 3A:
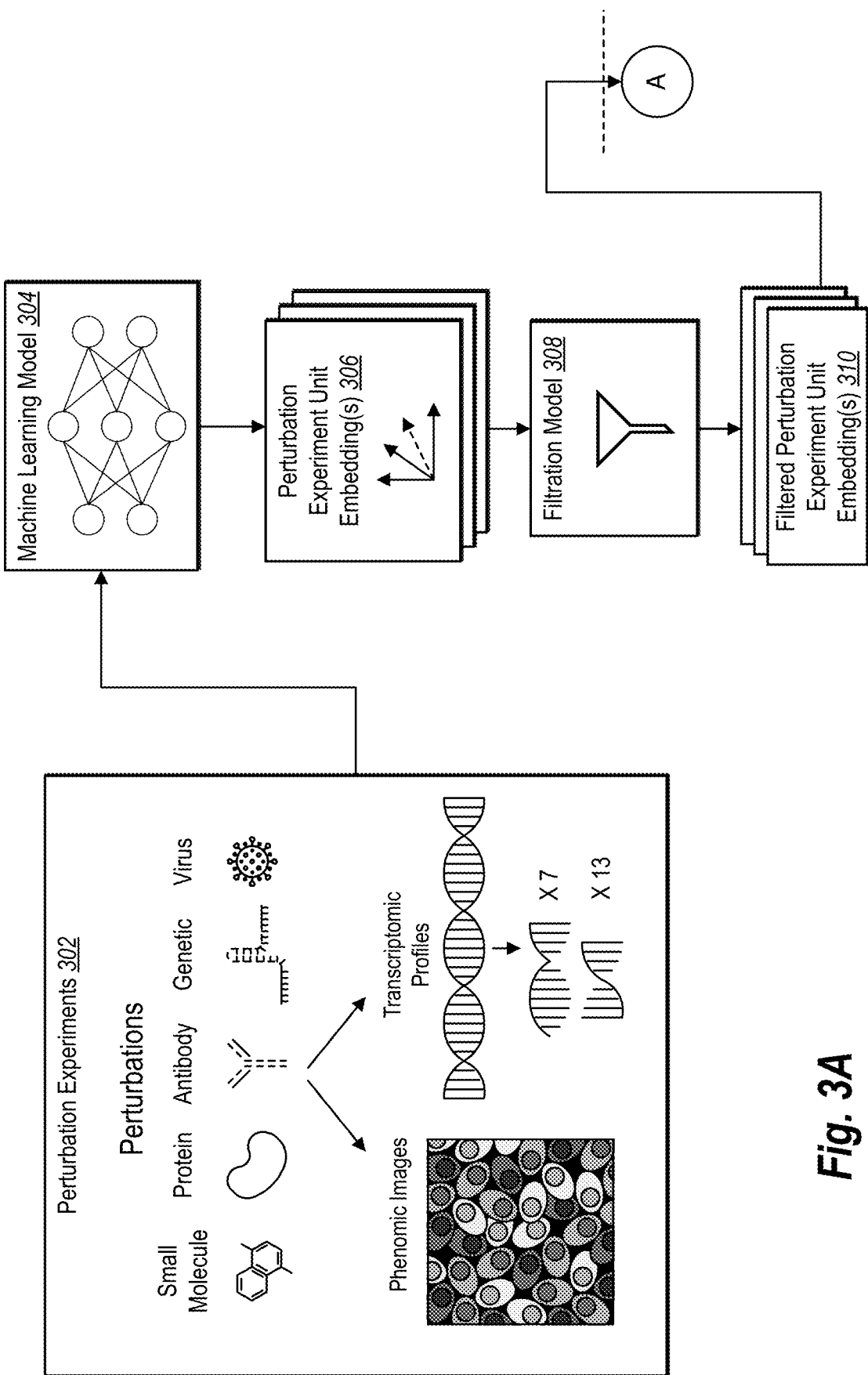
FIGS. 3A-3C illustrate providing similarity measures to a client device by using a machine learning model to embed perturbation data into a low dimensional space and applying various filtration, alignment, aggregation, and relation models to the data in accordance with one or more embodiments.

As mentioned above, the machine learning mapping system 106 can receive perturbation data and embed the perturbation data via the machine learning model 204 as discussed further with respect to FIG. 3A. For example, the machine learning mapping system 106 receives perturbation experiment unit measurements from perturbation experiments. For example, a perturbation experiment unit includes a unit (e.g., the smallest unit) that is measured in the particular experiment. The measurement of the perturbation experiment unit differs according to the perturbation experiment. The machine learning mapping system 106 can embed the perturbation experiment unit measurement in a lower dimensional space by embedding the perturbation experiment unit via the machine learning model 204. The different types of perturbation experiments and corresponding perturbation experiment units and measurements will be discussed in further detail with respect to FIG. 3A.

Figure 3B:
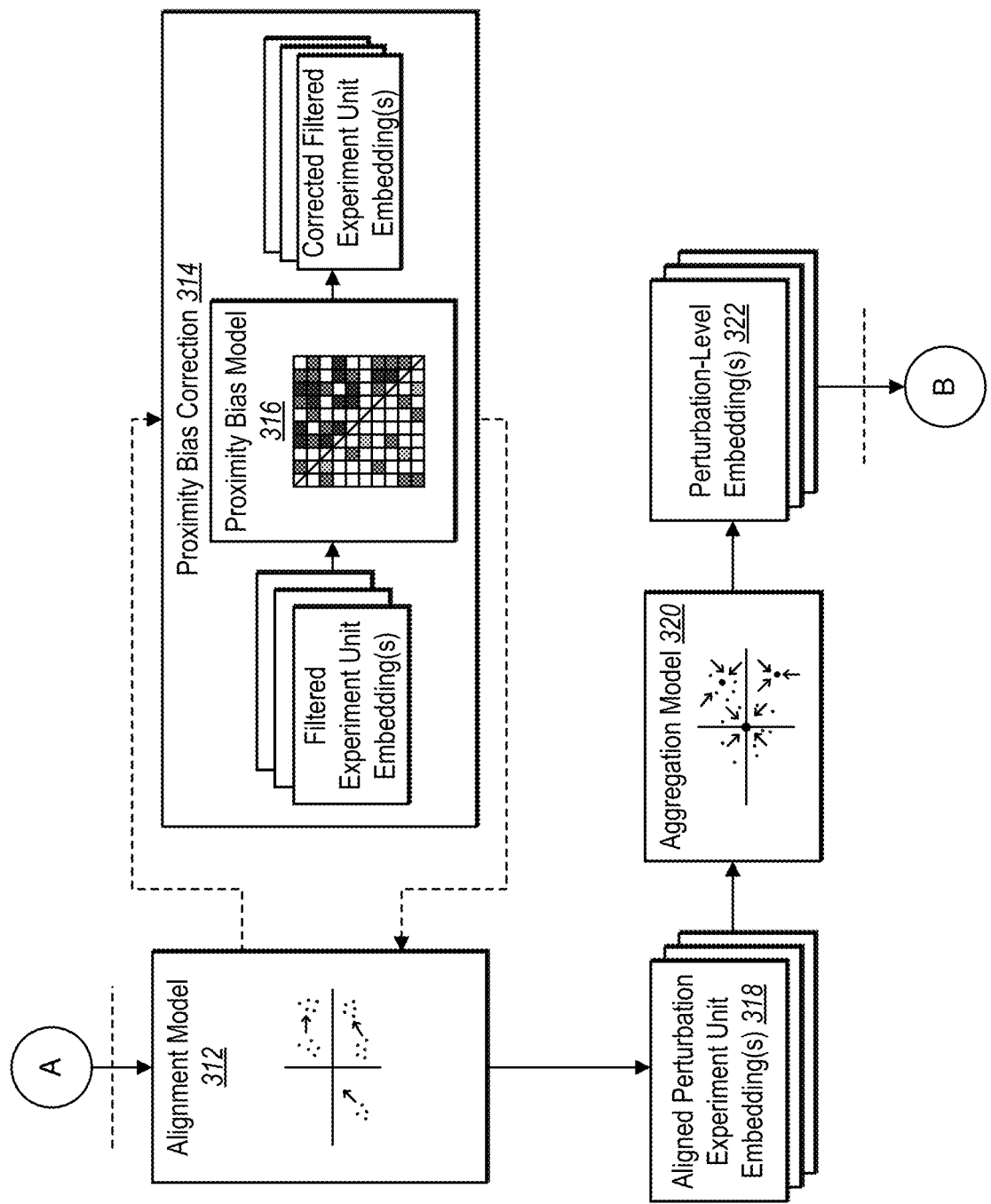
Figure 3C:
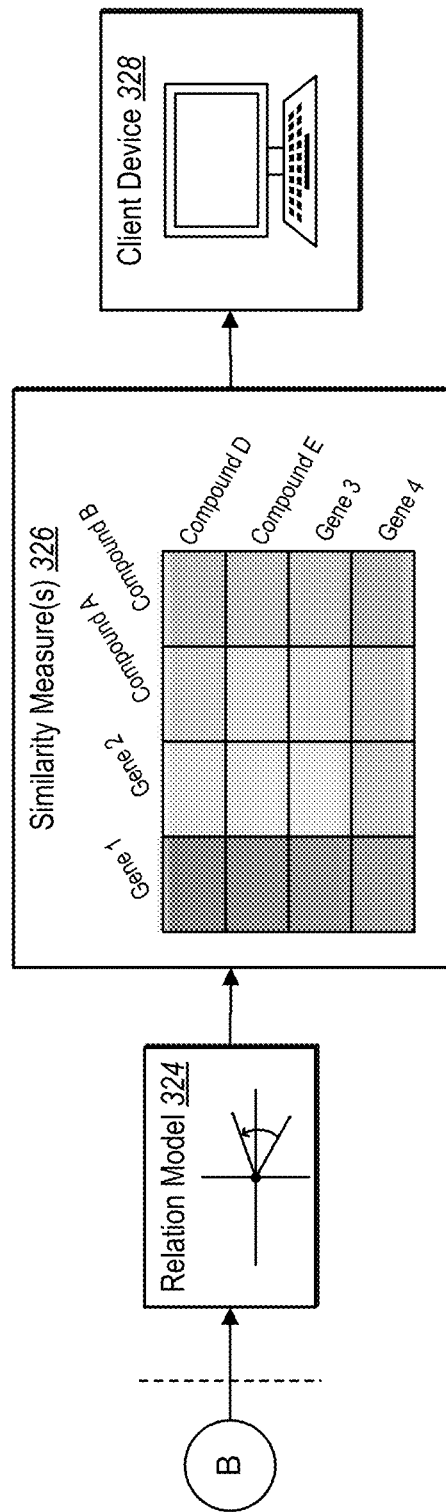

Further, as mentioned above, the machine learning mapping system 106 can apply various models such as a filtration model 206a, an alignment model 206b, an aggregation model 206c, and a relation model 206d to the perturbation experiment unit embeddings as discussed in further detail with respect to FIGS. 3A-3C. For example, the machine learning mapping system 106 uses a filtration model 206a to filter perturbation experiment unit embeddings according to various quality criteria. Moreover, the machine learning mapping system 106 uses an alignment model 206b to align the perturbation experiment unit embeddings the individual perturbation classes both within and across perturbation experiments according to a statistical alignment analysis. Additionally, the machine learning mapping system 106 uses an aggregation model 206c to generate the aligned perturbation experiment unit embeddings to generate a perturbation-level embedding for each perturbation class. Furthermore, the machine learning mapping system 106 uses a relation model 206d to generate similarity measures 208 (e.g., perturbation comparisons) using the perturbation-level embeddings of the perturbation classes.

Figure 4:
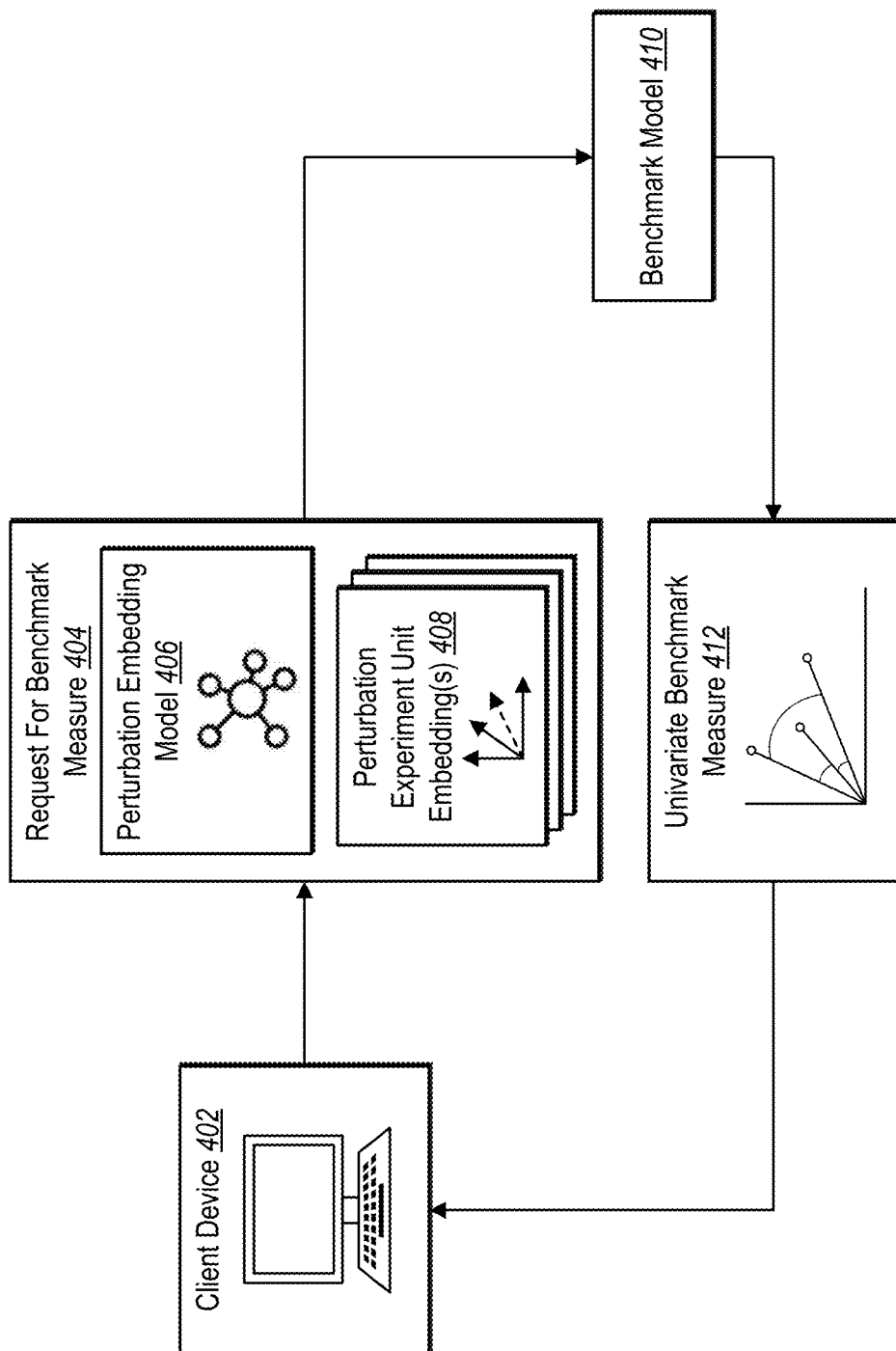
FIG. 4 illustrates determining, utilizing a benchmark model, a univariate benchmark measure for a perturbation embedding model and corresponding perturbation data in accordance with one or more embodiments.
Figure 5:
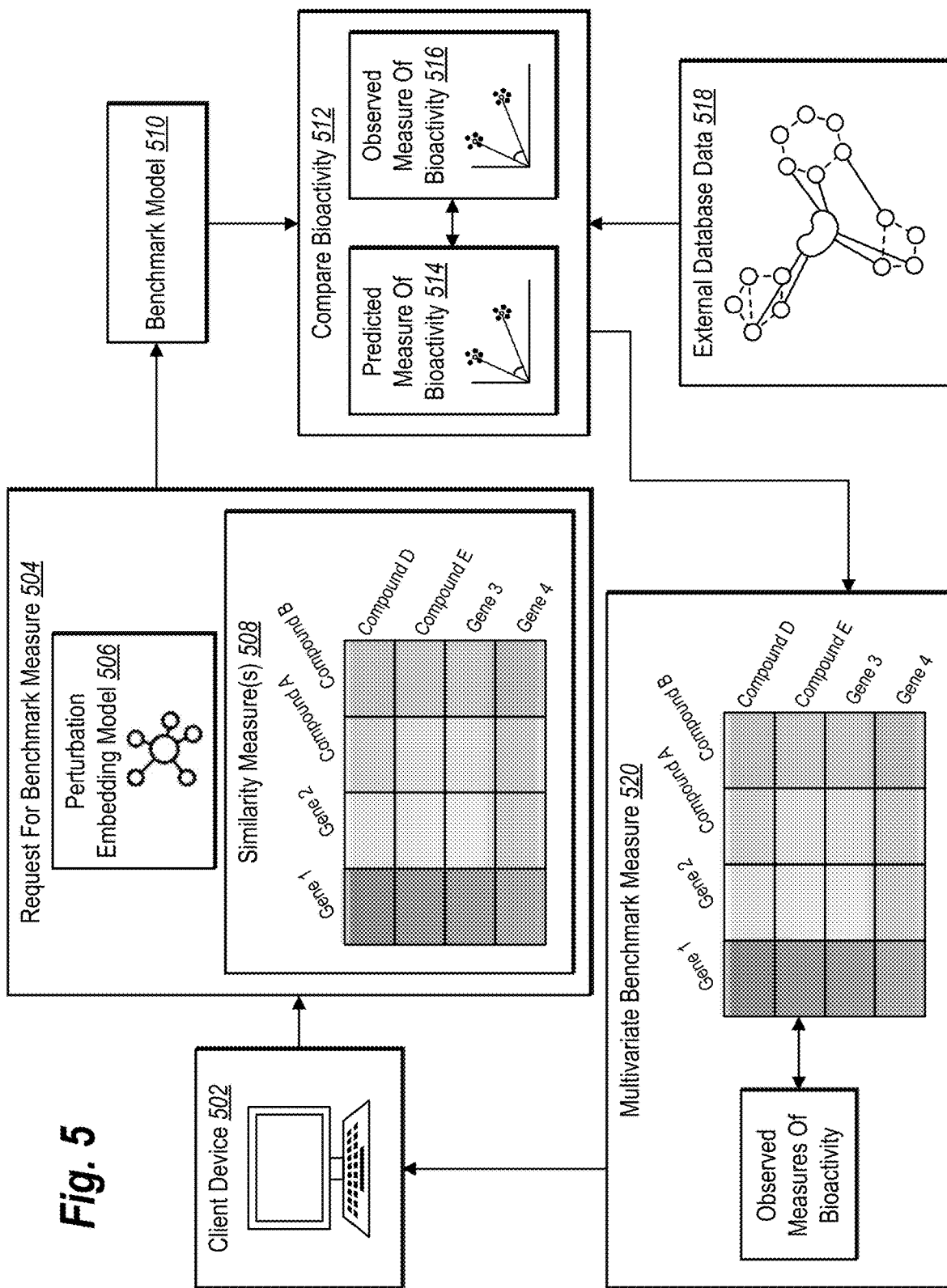
FIG. 5 illustrates determining, utilizing a benchmark model, a multivariate benchmark measure for a perturbation embedding model and corresponding perturbation data in accordance with one or more embodiments.

Moreover, the machine learning mapping system 106 can use a benchmark model 210 to determine a univariate benchmark measure 212 and/or a multivariate benchmark measure 214 for the perturbation data 202, as discussed in further detail with respect to FIGS. 4-5. For example, the machine learning mapping system 106 uses the benchmark model 210 to determine a univariate benchmark measure 212 by comparing the perturbation experiment unit embeddings of a perturbation class to one another or to a set of non-perturbation control embeddings. In another example, the machine learning mapping system 106 uses the benchmark model 210 to generate a multivariate benchmark measure 214 by comparing a predicted measure of bioactivity between perturbation classes (e.g., cell perturbation classes or other perturbation classes) to an observed measure of bioactivity between the perturbation classes. Further, the machine learning mapping system 106 provides the univariate benchmark measure and/or multivariate benchmark measure for display via a user interface of a client device as discussed with respect to FIG. 6.

In some embodiments, the machine learning mapping system 106 uses embeddings from any point in the embedding, filtration, alignment, aggregation, or relation of embeddings process to generate benchmark measures. For example, although FIG. 2 illustrates the machine learning mapping system 106 using perturbation experiment unit embeddings from before the filtration model 206a or after the relation model 206d, the machine learning mapping system 106 can utilize embeddings generated from any step or act to generate the univariate benchmark measure 212 and/or the multivariate benchmark measure 214 with the benchmark model 210. Indeed, the machine learning mapping system 106 can generate benchmark measures using the embeddings after filtering the embeddings with the filtration model 206a, after aligning the embeddings with the alignment model 206b, or after aggregating the embeddings with the model 206c.

As discussed above, the machine learning mapping system 106 can provide similarity measures between perturbation classes to a client device by using a machine learning model to embed the perturbation data and applying various models to the data. For example, FIGS. 3A-3C illustrate providing similarity measures 326 to a client device 328 by using a machine learning model 304 to embed perturbation data into a low dimensional space and applying various filtration, alignment, aggregation, and relation models to the data in accordance with one or more embodiments. Specifically, FIG. 3A illustrates generating filtered perturbation experiment unit embeddings 310 from data received from perturbation experiments 302 via the machine learning model 304 and a filtration model 308. Further, FIG. 3B illustrates generating perturbation-level embeddings 322 via an alignment model 312, a proximity bias model 316, and an aggregation model 320. Moreover, FIG. 3C illustrates applying a relation model 324 to the perturbation-level embeddings 322 and providing similarity measures 326 to a client device 328.

As mentioned above, FIG. 3A illustrates generating filtered perturbation experiment unit embeddings 310 from data received from perturbation experiments 302 via the machine learning model 304 and a filtration model 308 in accordance with one or more embodiments. Specifically, the machine learning mapping system 106 receives perturbation data from one or more perturbation experiments 302. Further, the machine learning mapping system 106 embeds the perturbation data into perturbation experiment unit embeddings 306 via the machine learning model 304. Additionally, the machine learning mapping system 106 generates filtered perturbation experiment unit embeddings 310 using a filtration model 308 to filter the perturbation experiment unit embeddings 306 according to various quality criteria.

As just mentioned, the machine learning mapping system 106 can receive perturbation data from one or more perturbation experiments 302. In particular, the machine learning mapping system 106 receives perturbation data from the perturbation experiments 302 by applying different perturbations to different cells (e.g., in wells of different plates) or to different in vivo subjects. A perturbation experiment refers to a process for applying a perturbation to a cell or a subject. A perturbation experiment also includes a process for developing/growing the perturbed cell into a resulting phenotype or a process for administering a perturbation to a subject in an in vivo perturbation experiment. Moreover, the machine learning mapping system 106 performs perturbation experiments that include thawing cells, plating them, transfection (e.g., in the case of CRISPR-treated wells, viral perturbations, or antibody perturbations), adding compounds or soluble factors, fixation, staining, and imaging. Additionally, the machine learning mapping system 106 performs perturbation experiments by administering a compound to a subject, observing the subject via digital video, and determining digital biomarkers via computer vision algorithms. Further, as used herein, the term well refers depression or area of a plate used to conduct an in vitro experiment. For example, a well refers to a depression or cavity in a microplate or multi-well plate. A well can serve as a testing or experimental chamber for samples, reagents, or substances. Thus, a well can hold one or more cells within a perturbation experiment.

Additionally, as used herein, the term "perturbation" (e.g., cell perturbation) refers to an alteration or disruption to a cell or the cell's environment (to elicit potential phenotypic changes to the cell). In particular, the term perturbation can include a small molecule perturbation (also referred to herein as a compound perturbation), a protein perturbation, an antibody perturbation, a gene perturbation, a virus perturbation, or an in vivo perturbation.

Moreover, a compound perturbation can include a cell perturbation using a molecule and/or soluble factor. For instance, a compound perturbation can include reagent profiling such as applying a small molecule to a cell and/or adding soluble factors to the cell environment. Additionally, a compound perturbation can include a cell perturbation utilizing the compound or soluble factor at a specified concentration. Indeed, compound perturbations performed with differing concentrations of the same molecule/soluble factor can constitute separate compound perturbations. A soluble factor perturbation is a compound perturbation that includes modifying the extracellular environment of a cell to include or exclude one or more soluble factors. Additionally, soluble factor perturbations can include exposing cells to soluble factors for a specified duration wherein perturbations using the same soluble factors for differing durations can constitute separate compound perturbations.

Additionally, a protein perturbation can include the alteration or modulation of the activity, expression, or function of a specific protein within a cell. For instance, a protein perturbation can include applying a molecule to the cell to determine an effect of the molecule on the protein. Effects on the protein can include inhibition, activation, stabilization, destabilization, alteration of protein-protein interactions, modulation of protein expression, etc.

Furthermore, an antibody perturbation can include the application of an antibody (or antibodies) to specifically target and modulate the activity of proteins or other biomolecules within a cell. Indeed, the antibody can be selected to interact with particular targets, such as proteins or other biomolecules associated with a particular disease. Moreover, effects of an antibody perturbation within the cell can include targeted inhibition of a protein, immunomodulation, etc.

Further, a gene perturbation can include gene-knockout perturbations (performed through a gene knockout experiment). For instance, a gene perturbation includes a gene-knockout in which a gene (or set of genes) is inactivated or suppressed in the cell (e.g., by CRISPR-Cas9 editing).

Additionally, a virus perturbation can include intentional introduction and/or manipulation of a virus into a cell or cell environment. For example, a virus perturbation can include introducing a virus into a cell or cell environment to determine virus interactions or identify potential antiviral drugs or therapeutic strategies. Indeed, a virus perturbation can include modeling viral infections, identifying host factors needed for the viral life cycle, etc.

Moreover, an in vivo perturbation can include administering a compound to an in vivo subject. Further, a compound may be administered to different subjects at different concentrations wherein each concentration of a compound can be considered a unique in vivo perturbation.

Thus, for example, an in vitro perturbation experiment can include a slide whereon a first well including stem cells with gene perturbations (e.g., CRISPR knockout of a particular gene), a second well including cells with compound perturbations (e.g., application of a particular drug), a third well including cells with protein perturbations, a fourth well including cells with antibody perturbations, and a fifth well including cells with viral perturbations. Additionally, an in vivo perturbation experiment can include a first subject or group of subjects receiving a first in vivo perturbation and a second subject or group of subjects receiving a second in vivo perturbation.

Moreover, the machine learning mapping system 106 can receive perturbation data in a variety of measurement types such as phenomic images, transcriptomic profiles, invivomic profiles, etc. to compliment the specific perturbation. For example, the machine learning mapping system 106 can receive perturbation data by utilizing a high-dimensional digital camera to capture digital images of cells portraying different phenotypes resulting from the different perturbations. These phenomic images thus illustrate the resulting cellular effects of the underlying perturbations. Moreover, the machine learning mapping system 106 can receive perturbation data by utilizing sequencing equipment to generate transcriptomic profiles. These transcriptomic profiles include mRNA transcript counts for genes of interest. Thus, the transcriptomic profiles illustrate the effects of the underlying perturbation on the transcriptome of the treated cells. Further, a transcriptomic profile can be generated via a variety of methods including perturbation of a single cell such as via a gene knockout using CRISPR or via perturbation of many cells such as in a single container or in wells of a plate. Additionally, the machine learning mapping system 106 can receive perturbation data by utilizing digital cameras to capture continuous video of a subject's environment and computer vision algorithms to calculate digital biomarkers (e.g., breathing and motion) to generate invivomic profiles. An invivomic profile can include one or more digital biomarker observations of a subject. For example, digital biomarkers include breathing patterns, motion patterns, etc. Thus, the invivomic profiles illustrate the effects of a perturbation on a subject. In some implementations, the machine learning mapping system 106 receives multimodal perturbation data from the same cells. For example, the multimodal perturbation data can include phenomic images and transcriptomic profiles acquired from the same cells. Indeed, the machine learning mapping system 106 can receive any two or more perturbation data types that are compatible (i.e., that can be measured from the same cells or subjects).

Further, an experimental entity (e.g., the smallest experimental entity) that the machine learning mapping system 106 measures in a perturbation experiment 302 is referred to as a perturbation experiment unit. Indeed, a perturbation experiment unit can be a single cell, a well with hundreds of cells, a portion of a well, an entire plate of wells, or some other division of cells or subjects. For example, a perturbation experiment unit in a gene perturbation can include a single cell, a perturbation experiment unit in a compound perturbation can include a well with hundreds of cells, a perturbation experiment unit in an in vivo perturbation can include a single subject or a collection of subjects, etc.

Moreover, the machine learning mapping system 106 can repeatedly perform the cell perturbation experiments 302 and collect the perturbation data therefrom. For example, in some implementations, the machine learning mapping system 106 performs these acts millions of times (per week) to generate digital phenomic images, transcriptomic profiles, and invivomic profiles portraying perturbations from consistent experimental protocols that can then be compared for determining relationships between the underlying genes, compounds, proteins, antibodies, and/or viruses at issue. Thus, the machine learning mapping system 106 can receive perturbation experiment unit measurements (also referred to herein simply as perturbation experiment units) from a plurality of wells, cells, or subjects corresponding to a plurality of cell perturbations. Additionally, the wells can be located on a plurality of plates and from a plurality of separate perturbation experiments.

Further, as shown in FIG. 3A, the machine learning mapping system 106 embeds the perturbation data into perturbation experiment unit embeddings 306 via the machine learning model 304. In particular, the machine learning mapping system 106 generates perturbation experiment unit embeddings utilizing the machine learning model 304. Indeed, the machine learning mapping system 106 generates a perturbation experiment unit embedding for each perturbation experiment unit received from the perturbation experiments 302 utilizing the machine learning model 304. Indeed, As used herein, the term "perturbation experiment unit embedding" refers to a numerical representation of a perturbation experiment unit measurement. For example, a perturbation embedding includes a vector representation of a phenomic image, a transcriptomic profile, or an invivomic profile generated by a machine learning model (e.g., a convolutional neural network or other machine learning embedding model). Thus, a perturbation experiment unit embedding includes a feature vector generated by application of various convolutional neural network layers (at different resolutions/dimensionality).

The machine learning mapping system 106 can utilize a variety of machine learning models to generate the perturbation experiment unit embeddings 306. For instance, in some embodiments, the machine learning mapping system 106 utilizes a deep learning model such as a deep image embedding model (e.g., a neural network such as a convolutional neural network) or a foundation model. For example, upon capturing unstructured data such as phenomic images, the machine learning mapping system 106 utilizes a deep image embedding model or foundation model to generate phenomic image embeddings. In another example, upon generating structured data such as transcriptomic profiles, the machine learning mapping system 106 utilizes the deep learning model to generate transcriptomic profile embeddings. In a further example, upon generating invivomic profiles, the machine learning mapping system 106 utilizes the deep learning model to generate invivomic embeddings. For instance, a deep image embedding model or deep learning model includes a neural network (e.g., a convolutional neural network), a foundation model, or other embedding model that generates a vector representation of an input digital image. In one or more implementations, the machine learning mapping system 106 utilizes a model described in UTILIZING MASKED AUTO ENCODER GENERATIVE MODELS TO EXTRACT MICROSCROPY REPRESENTATION AUTOENCODER EMBEDDINGS, U.S. application Ser. No. 18/545,399, filed Dec. 19, 2023, which is incorporated by reference in its entirety herein.

In some implementations, the machine learning mapping system 106 trains the deep learning model/s through supervised learning (e.g., to predict perturbations from digital images). For instance, the machine learning mapping system 106 trains the deep learning model to generate predicted perturbations from phenomic images, transcriptomic profiles, invivomic profiles, or other perturbation data. For instance, the machine learning mapping system 106 utilizes neural network layers to generate vector representations of the perturbation experiment units at different levels of abstraction and then utilizes output layers to generate predicted perturbations. The machine learning mapping system 106 then trains the deep learning model by comparing the predicted perturbations with ground truth perturbations.

With regard to FIG. 3A, the machine learning mapping system 106 utilizes the machine learning model 304 to generate perturbation experiment unit embeddings (e.g., feature/vector representations) of new perturbation experiment unit measurements. For instance, the machine learning mapping system 106 utilizes the internal neural network layers to generate embeddings (rather than generate perturbation predictions). The machine learning mapping system 106 then utilizes the embeddings as representations of the perturbation experiment units.

Thus, utilizing the convolutional neural network, the machine learning mapping system 106 can embed each perturbation experiment unit into a low dimensional feature space. Indeed, the machine learning mapping system 106 generates a multi-dimensional representation of each image within the low dimensional feature space. These multi-dimensional representations thus represent the features of different underlying perturbations (e.g., compounds, proteins, antibodies, gene knockouts, and/or viruses) as reflected in phenomic images utilized to generate the embeddings.

Additionally, the machine learning mapping system 106 generates filtered perturbation experiment unit embeddings 310 using a filtration model 308 to filter the perturbation experiment unit embeddings 306 according to various quality criteria. In particular, the machine learning mapping system 106 applies a filtration model 308 to filter each perturbation experiment unit embedding 306 according to one or more quality criterion. In particular, the machine learning mapping system 106 utilizes quality criteria in the filtration model 308 to filter outlier embeddings. As used herein, the term filtration model refers to a model that removes or filters data points. For example, a filtration model includes a computer-implemented model that removes perturbation experiment unit embeddings measurements or embeddings from a dataset. To illustrate, a filtration model can apply one or more quality criterion and remove digital images or embeddings that fail to satisfy the quality criterion. Relatedly, as used herein, the term "quality criterion" refers to a metric or measure of quality (e.g., of a perturbation experiment unit measurement or embedding). For instance, quality criterion can include a measure of completeness, clarity, cell count, consistency and/or behavior of a subject. Thus, for example, if a phenomic image (a digital image) of a well is blank or an in vivo subject shows no change in behavior, the machine learning mapping system 106 can apply the filtration model to remove the perturbation experiment unit from a dataset. Further, in some instances the machine learning mapping system 106 can receive phenomic image patches (images of a portion of a well) to which the machine learning mapping system 106 can apply the filtration model to remove biases based on location within the well. In another example, the machine learning mapping system 106 can apply the filtration model to remove perturbation experiment units exhibiting off target effects resulting from CRISPR guides which cause DNA to be cut in unintended places. Similarly, if an embedding fails to meet certain consistency metrics, the machine learning mapping system 106 can apply the filtration model to withhold the embedding from further processes, such as alignment, aggregation, etc.

Although FIG. 3A illustrates applying the filtration model 308 to the perturbation experiment unit embeddings 306 it will be appreciated that the machine learning mapping system 106 can apply the filtration model 308 to the perturbation experiment units. For example, in some implementations, the machine learning mapping system 106 applies the filtration model 308 directly to perturbation experiment units such as phenomic images, transcriptomic profiles, or invivomic profiles prior to embedding the measurements via the deep learning model.

In some implementations, the machine learning mapping system 106 applies the filtration model 308 to perturbation experiment unit embeddings 306 and/or perturbation-level embeddings 322 based on consistency criteria. For example, the machine learning mapping system 106 can apply a phenoprint filter/consistency filter to ensure that vector representations for a particular perturbation are consistently providing reliable information. For example, in one or more implementations, the machine learning mapping system 106 filters out embeddings (utilizing a phenoprint filter), if vector representations of different guides for a gene are not consistently pointing to the same direction in the perturbation representation space.

To illustrate, in some implementations, the machine learning mapping system 106 defines the center of the perturbation feature space relative to non-coding intron genes. Thus, the center of the space is the center of a certain number of intron wells (e.g., perturbation experiment units resulting from cell perturbations corresponding to these introns). Accordingly, the perturbation embeddings are defined relative to how the introns appear in the embedding space. Accordingly, genes can be flagged utilizing the phenoprint filter if the resulting vector representations fail to satisfy a threshold consistency (e.g., fail to point within a threshold direction) relative to the center of the embedding space.

Moreover, in one or more embodiments, the machine learning mapping system 106 can utilize a variety of the univariate benchmark measures discussed herein for filtration. For example, the machine learning mapping system 106 can utilize the filtration model 308 to apply the methods for determining the univariate benchmark measures as described below with respect to FIG. 4. Thus, in these or other embodiments, the machine learning mapping system 106 uses the filtration model 308 to filter perturbation experiment unit embeddings that fail to meet a required threshold of a univariate benchmark measure.

Further, as mentioned previously, FIG. 3B illustrates generating perturbation-level embeddings 322 via an alignment model 312, a proximity bias model 316, and an aggregation model 320 in accordance with one or more embodiments. Specifically, the machine learning mapping system 106 uses the alignment model 312 to generate aligned perturbation experiment unit embeddings 318 from the filtered perturbation experiment unit embeddings 310. As part of the alignment model 312, the machine learning mapping system 106 performs proximity bias correction 314 of the filtered perturbation experiment unit embeddings 310 using a proximity bias model 316. Further, the machine learning mapping system 106 generates perturbation-level embeddings 322 from the aligned perturbation experiment unit embeddings 318 using the aggregation model 320.

As just mentioned, the machine learning mapping system 106 can use the alignment model 312 to generate aligned perturbation experiment unit embeddings 318 from the filtered perturbation experiment unit embeddings 310. For example, the machine learning mapping system 106 aligns the perturbation experiment unit embeddings 310 for each perturbation class using the statistical alignment model 312. The perturbation class encompasses the biological replicates (and the corresponding embeddings) of a single perturbation whether within a single perturbation experiment 302 or across multiple perturbation experiments 302. For example, the embeddings of a first compound perturbation of a cell or cells can constitute a first perturbation class, the embeddings of a second compound perturbation of a cell or cells can constitute a second perturbation class, the embeddings of a first gene perturbation of a cell or cells can constitute a third class, the embeddings of a first antibody perturbation of a cell or cells can constitute a fourth perturbation class, etc.

As used herein, the term alignment model refers to a model that aligns or corrects datapoints. In particular, an alignment model includes a computer-implemented algorithm for aligning embeddings to remove artifacts, irregularities, or skewing factors, such as batch effects. The machine learning mapping system 106 can utilize a variety of alignment models, including centerscale (e.g., per-batch standardization), TVN (typical variation normalization), or other alignment approaches (e.g., nearest neighbor matching or conditional variational autoencoders). In one or more implementations, the machine learning mapping system 106 aligns datapoints utilizing a proximity bias model as discussed in further detail below.

For example, the machine learning mapping system 106 can utilize various models to reduce or eliminate non-biological sources of variation in data. For instance, the machine learning mapping system 106 can utilize various normalization approaches such as quantile normalization or TMM normalization. Moreover, the machine learning mapping system 106 can utilize match effect removal models, such as ComBat or Surrogate Variable Analysis.

In one or more implementations, the machine learning mapping system 106 utilizes a baseline approach for aligning perturbation experiment unit embeddings by using control units in each batch to center and scale features in each set. For example, the machine learning mapping system 106 can include a control unit of the same cell/perturbation combination in each batch. The machine learning mapping system 106 can then align each batch by aligning the control unit across batches. Thus, the machine learning mapping system 106 can utilize a variety of alignment models, including centerscale (e.g., per-batch standardization) or TVN (typical variation normalization). For example, the machine learning mapping system 106 can utilize the alignment model 312 to align perturbation experiment unit embeddings across perturbation experiments.

Thus, the machine learning mapping system 106 can analyze a plurality of perturbation experiment unit embeddings to generate aligned perturbation experiment unit embeddings. Specifically, in one or more implementations, the machine learning mapping system 106 aligns a set of perturbation experiment unit embeddings from a plurality of different perturbation experiments (having a shared perturbation class) according to a statistical alignment model, as described above.

As mentioned previously, the machine learning mapping system 106 can perform proximity bias correction 314 of the filtered perturbation experiment unit embeddings 310 using a proximity bias model 316 to generate proximity bias corrected perturbation experiment unit embeddings. Proximity bias, as used herein, refers to a bias or skewing resulting from CRISPR gene knockouts. In particular, proximity bias includes the systematic phenotypic similarity of CRISPR-Cas9 knockouts to knockouts of biologically unrelated genes on the same chromosome arm. For example, the distribution of similarities (e.g., cosine similarities) for relationships between genes on the same chromosome is shifted relative to the distribution of similarities for gene pairs on different chromosomes. The proximity bias model 316 can correct for proximity bias utilizing a vector representation of the proximity bias. In particular, the proximity bias model 316 can determine a vector representation of unexpressed genes of a chromosome arm (e.g., perturbation experiment unit embeddings of the unexpressed genes) and utilize the vector representation to correct for proximity bias. For instance, the proximity bias model 316 can apply the vector correction representation to a perturbation experiment unit embedding to generate a corrected perturbation experiment unit embedding. To illustrate, in one or more implementations, the proximity bias model 316 determines and subtracts a mean vector for unexpressed genes of a chromosome arm from each gene representation (e.g., perturbation experiment unit embedding) on that arm. Indeed, in one or more embodiments, the machine learning mapping system 106 can utilize a proximity bias model as described in High-Resolution Genome-wide Mapping of Chromosome-arm-scale Truncations Induced by CRISPR-Cas9 Editing published in bioRxiv on Apr. 15, 2023, the contents of which are herein incorporated by reference in their entirety. Accordingly, the machine learning mapping system 106 can utilize the proximity bias model 316 to generate proximity bias corrected perturbation experiment unit embeddings.

By utilizing the proximity bias model 316, the machine learning mapping system 106 can generate corrected perturbation experiment unit embeddings (e.g., corrected perturbation experiment unit embeddings and ultimately corrected perturbation-level perturbation experiment unit embeddings). Thus, the machine learning mapping system 106 generates, utilizing the proximity bias model 316, proximity bias corrected perturbation-level perturbation experiment unit embeddings. Moreover, as described in greater detail below, the machine learning mapping system 106 can also generate perturbation comparisons from the proximity bias corrected perturbation-level perturbation experiment unit embeddings.

Further, the machine learning mapping system 106 can aggregate the aligned perturbation experiment unit embeddings 318 to generate perturbation-level embeddings 322 using the aggregation model 320. As used herein, the term aggregation model refers to a computer-implemented model for combining or aggregating data points. For example, an aggregation model includes a computer-implemented model for combining or aggregating embeddings (e.g., perturbation experiment unit embeddings). Thus, an aggregation model can transform embeddings from one level to another level. To illustrate, an aggregation model can combine a plurality of patch embeddings from a well to generate well-level embeddings. Moreover, an aggregation model can combine a plurality of perturbation experiment unit embeddings for a particular perturbation to generate perturbation-level embeddings (i.e., an embedding representing a perturbation generated by combining individual perturbation experiment unit embeddings representing a perturbation class). Similarly, the aggregation model can generate experiment-level embeddings (e.g., by combining perturbation experiment unit embeddings for a particular experiment).

Furthermore, as mentioned above, in some implementations the machine learning mapping system 106 can apply the aggregation model 320 to the aligned perturbation experiment unit embeddings to generate the perturbation-level image embedding 322 for each perturbation class. Indeed, each perturbation class can include at least several biological replicates within an experiment, resulting in replicate perturbation experiment unit embeddings for each perturbation class. Additionally, disparate perturbation experiments may also include replicate perturbations resulting in additional perturbation experiment unit embeddings for each perturbation class. Once the machine learning mapping system 106 aligns these replicates, as described above, the machine learning mapping system 106 can then apply the aggregation model 320 to the aligned perturbation experiment unit embeddings to generate the perturbation-level image embedding 322 for each perturbation class.

The machine learning mapping system 106 can utilize a variety of aggregation approaches. In some implementations, the machine learning mapping system 106 utilizes a mean or averaging approach. For example, the machine learning mapping system 106 determines feature vectors (e.g., perturbation experiment unit embeddings) and averages the feature vectors for a particular perturbation class to generate a perturbation-level image embedding. Thus, in some implementations, the machine learning mapping system 106 can utilize an aggregation model that calculates the mean adjusted perturbation experiment unit embeddings to generate the perturbation-level image embeddings. The machine learning mapping system 106 can utilize other aggregation approaches. For example, the machine learning mapping system 106 can also utilize a weighted combination approach (e.g., that weights different embeddings differently based on features or characteristics, such as recency, image quality, image source, etc.). Similarly, the machine learning mapping system 106 can utilize other statistical aggregation models. Moreover, the machine learning mapping system 106 can generate, and provide for display via the client device 328, a confidence measure for each perturbation-level embedding 322 generated by the aggregation model 320.

The machine learning mapping system 106 can aggregate at a variety of different levels (e.g., levels of features, specificity, or detail) for generating aggregated embeddings. Although FIG. 3B illustrated perturbation-level embeddings, the aggregation model 320 can aggregate based on different features, such as according to well (e.g., aggregate embeddings in the same well of an experiment), gene (e.g., aggregate embeddings corresponding to a particular gene), gene guide (e.g., aggregate according to a particular CRISPR gene-guide), pathway (e.g., protein pathways), and/or mechanism of action (e.g., biochemical interactions through which a compound produces an effect). By aggregating according to these features, the machine learning mapping system 106 can generate perturbation-level embeddings (e.g., for gene perturbations or compound perturbations), well-level embeddings, gene-level embeddings, pathway-level embeddings, or mechanism of action embeddings.

In one or more implementations, the machine learning mapping system 106 can also update the perturbation-level embeddings with updated embeddings (e.g., upon capturing additional perturbation images and generating additional perturbation experiment unit embeddings). For instance, the machine learning mapping system 106 receives an additional plurality of perturbation experiment unit measures portraying additional cells. In response, the machine learning mapping system 106 generates, utilizing the machine learning model 304, an additional plurality of perturbation experiment unit embeddings. Moreover, the machine learning mapping system 106 generates modified perturbation-level image embeddings from the additional plurality of perturbation experiment unit embeddings and the (original) perturbation experiment unit embeddings. In particular, the machine learning mapping system 106 combines the original perturbation experiment unit embeddings and the additional (new) perturbation experiment unit embeddings by utilizing the alignment model 312 and the aggregation model 320 (as described above).

Furthermore, in one or more embodiments, the machine learning mapping system 106 can utilize varying versions of the models described above (e.g., the filtration model 308, the alignment model 312, the aggregation model 320, the proximity bias model 316), or may eliminate, reorder, or repeat one or more of these models to generate perturbation-level embeddings.

Indeed, in one or more implementations, the machine learning mapping system 106 performs a different order than illustrated in FIGS. 3A-3B by first aligning, then filtering, then aggregating. Similarly, in some implementations, the machine learning mapping system 106 applies multiple different aggregation processes. For example, the machine learning mapping system 106 can aggregate from guide-level to gene-level embeddings. Similarly, the machine learning mapping system 106 can aggregate across experiment repeats. Moreover, the machine learning mapping system 106 can apply filtration models multiple times, at different stages, utilizing different filter criterion.

Moreover, as mentioned above, FIG. 3C illustrates applying a relation model 324 to the perturbation-level embeddings 322 and providing similarity measures 326 to a client device 328 in accordance with one or more embodiments. Indeed, the machine learning mapping system 106 utilizes the relation model 324 to generate similarity measures 326 from the perturbation-level embeddings 322. Further, the machine learning mapping system 106 provides the similarity measures 326 for display to the client device 328.

As mentioned, the machine learning mapping system 106 utilizes the relation model 324 to generate similarity measures 326 from the perturbation-level embeddings 322. As used herein, the term relation model refers to a model that relates data points to each other. For example, a relation model includes a computer-implemented model that determines a similarity measure between embeddings. To illustrate, the machine learning mapping system 106 can utilize a relation model to determine a similarity between perturbation-level embeddings for phenomic images, transcriptomic profiles, or in vivo observations. Relatedly, the term "similarity measure," as used herein, refers to a metric or value indicating likeness, relatedness, or similarity. For instance, a similarity measure includes a metric indicating relatedness between two perturbations (e.g., between two perturbation-level embeddings). To illustrate, the machine learning mapping system 106 can determine a similarity measure by comparing two feature vectors representing phenomic digital images, two transcriptomic profiles, or two in vivo observations. Thus, a similarity measure can include a cosine similarity between feature vectors or a measure of distance (e.g., Euclidian distance) in a feature space. Further, in some embodiments, the machine learning mapping system 106 can determine a similarity measure by passing the perturbation-level embeddings for different perturbation classes to a deep learning network trained on known biological relationships (such as known biological relationships sourced from external databases). Moreover, the machine learning mapping system 106 can utilize the relation model 324 to generate a variety of different similarity measures 326 from the perturbation-level embedding 322.

In one or more implementations, the machine learning mapping system 106 can utilize the relation model 324 to determine a projection or rejection similarity. The term "projection similarity," as used herein, refers to a measure comparing the magnitude of different embeddings (e.g., the magnitude of the component of the vector of a perturbation-level embedding for one perturbation class relative to the vector of a reference perturbation-level embedding of a separate perturbation class). More specifically, a projection similarity represents the magnitude of the component of a vector of the perturbation-level embedding for a given perturbation class in the direction of the vector of a reference perturbation-level embedding for a separate perturbation class. For instance, the machine learning mapping system 106 generates and provides a projection similarity to provide a magnitude and direction of a perturbation-level embedding for a perturbation class relative to a reference perturbation-level embedding. Indeed, the machine learning mapping system 106 utilizes any perturbation-level embedding as a reference in determining the projection similarity of a perturbation-level embedding for a perturbation class. To illustrate, the machine learning mapping system 106 utilizes a first perturbation-level embedding for a first perturbation class representing a gene perturbation as a reference perturbation-level embedding. Further, the machine learning mapping system 106 utilizes the reference perturbation-level embedding to determine projection similarity for a second perturbation-level embedding of a second perturbation class representing a compound perturbation. Further, the machine learning mapping system 106 utilizes vector decomposition calculations to determine the projection similarity between the two perturbation-level embeddings. Similarly, the machine learning mapping system 106 determines a rejection similarity utilizing the relation model 324. The term "rejection similarity," as used herein, represents the magnitude of the component of a vector of a perturbation-level embedding for a given perturbation class in the direction perpendicular to the direction of the vector of a reference perturbation-level embedding for a separate perturbation class. Moreover, the machine learning mapping system 106 determines a projection and/or rejection similarity when determining a benchmark measure for a perturbation embedding model as discussed further with respect to FIGS. 4 and 5.

As mentioned, the machine learning mapping system 106 can provide the similarity measures 326 for display via the client device 328. Indeed, the machine learning mapping system 106 generates a representation of the similarity measure for display on the client device 328. Further, the machine learning mapping system 106 generates a variety of representations of the similarity measures 326 including, by way of example, and not limitation, a heatmap (as shown in FIG. 3C), a map displaying numerical values, a table displaying numerical values, etc. Thus, the machine learning mapping system 106 provides the similarity measures to the client device 328 for display.

In some implementations, the machine learning mapping system 106 generates transcriptomic profiles for different perturbation classes and relate these transcriptomic profiles using a transcript relation model. Specifically, the machine learning mapping system 106 receives perturbation data from perturbation experiments 302 for high scale transcriptomics (i.e., high scale transcriptomic experiments). Further, the machine learning mapping system 106 utilizes a transcript analysis model to generate transcriptomic embeddings for each perturbation class. Moreover, the machine learning mapping system 106 utilizes a transcript relation model to determine relationships between the perturbation classes using the transcriptomic embeddings.

As just mentioned, the machine learning mapping system 106 can generate perturbation data from high scale transcriptomic experiments to generate transcriptomic profiles. For example, the machine learning mapping system 106 generates and/or receives the perturbation data from high scale transcriptomic experiments wherein a perturbation (or set of perturbations) is applied to the cells of a well in a plate such that each well is associated with a single perturbation (or set of perturbations). Further, the machine learning mapping system 106 generates the perturbation data (e.g., utilizing a gene sequencer), which includes a count of the mRNA transcripts associated with the cells of each well representing a perturbation class. For example, the machine learning mapping system 106 determines a count of the mRNA transcripts from each well associated with each perturbation class as determined by a unique, well-based oligonucleotide sequence that attaches to each molecule generated from the cells in each well. Accordingly, the machine learning mapping system 106 generates or receives the count of the mRNA transcripts for a gene annotation set (e.g., representing selected genes of interest such as protein coding genes for proteins of interest) generated by the cells associated with each perturbation class in response to the perturbation.

Additionally, the machine learning mapping system 106 generates a transcriptomic profile for each perturbation class. Indeed, the machine learning mapping system 106 utilizes the count of the mRNA transcripts for a gene annotation set associated with a specific perturbation class to generate the transcriptomic profile. For example, the machine learning mapping system 106 generates the transcriptomic profile for each perturbation class by generating a dataset in a table wherein each row header represents a perturbation experiment (or perturbation class) and each column header represents a unique gene of interest (the columns combined representing the gene annotation set). Further, the machine learning mapping system 106 populates the table with the mRNA count for each gene (column). Thus, each row of data represents the transcriptomic profile for each perturbation class including the set of mRNA counts across all the genes in the gene annotation set.

To illustrate, the machine learning mapping system 106 generates and/or receives the count of mRNA transcripts from a sequencer for a compound perturbation and a gene perturbation. Further, the machine learning mapping system 106 generates a table with the genes of the gene annotation set populating the columns of the table. Moreover, the machine learning mapping system 106 generates the transcriptomic profiles for the compound perturbation and the gene perturbation by generating populating the table with the mRNA transcript counts for each gene of the gene annotation set. Thus, the first row of the table represents the transcriptomic profile for the compound perturbation and the second row of the table represents the transcriptomic profile for the gene perturbation.

Further, as noted above, the machine learning mapping system 106 can utilize a transcript analysis model to generate transcriptomic embeddings for each perturbation class. Specifically, the machine learning mapping system 106 uses the transcript analysis model to deduplicate the transcript counts to account for PCR amplification used when generating the transcript counts such that each transcript count represents the estimated true transcript count. Further, the machine learning mapping system 106 utilizes the transcript analysis model to embed the transcriptomic profiles (with deduplicated transcript counts). As used herein, the term "transcript analysis model" refers to a statistical analysis for dimensional reduction. In particular, a transcript analysis model can include Principal Component Analysis (PCA), a machine learning model (e.g., convolutional neural network), or other analysis methods for dimensional reduction of high-dimensional data. For instance, the machine learning mapping system 106 utilizes the transcript analysis model to embed the transcriptomic profiles (i.e., generate transcriptomic embeddings) such that the transcriptomic embeddings include the principal components of the transcriptomic profiles.

To illustrate, the machine learning mapping system 106 utilizes the transcript analysis model to embed the transcriptomic profiles of the compound perturbation and the gene perturbation. For instance, each transcriptomic profile can include thousands of genes that have an above zero mRNA count and thousands of genes that have an mRNA count of zero. Thus, the machine learning mapping system 106 uses the transcript analysis model to remove the genes that have an mRNA count of zero from further analysis. Further, the machine learning mapping system 106 reduces the dimensionality of the compound and gene perturbation transcriptomic profiles to a lower dimensionality representation, i.e., the transcriptomic embedding, using the transcript analysis model. For example, the machine learning mapping system 106 uses the transcript analysis model to determine the principal components of the transcriptomic profiles for each of the compound and the gene perturbation to represent the respective transcriptomic profiles with a pre-determined low dimensional transcriptomic embedding (e.g., an embedding having 25 or 64 dimensions). Further, the machine learning mapping system 106 relates the transcriptomic embedding of the compound perturbation to the transcriptomic embedding of the gene perturbation to determine a similarity between the two.

As mentioned, the machine learning mapping system 106 can utilize a transcript relation model to determine relationships between the perturbation classes using the transcriptomic embeddings. As used herein, the term "transcript relation model" refers to a computer-implemented model for determining embedding vector relationships. In particular, the transcript relation model relates the transcriptomic embeddings of different perturbation classes to one another. For example, the machine learning mapping system 106 uses the transcript relation model to determine a similarity measure between the transcriptomic embeddings of different perturbation classes. Indeed, the machine learning mapping system 106 can use the transcript relation model to determine the similarity measure using any one of, or a combination of, methods for determining a similarity between transcriptomic embeddings including determining a cosine similarity, determining the Euclidean distance, determining correlation coefficients, variance comparison, etc.

To illustrate, the machine learning mapping system 106 uses the transcript analysis model to determine a relationship between the transcriptomic embedding of the compound perturbation and the gene perturbation discussed above. For example, upon generating the transcriptomic embeddings for the compound perturbation and the gene perturbation, the machine learning mapping system 106 determines a cosine similarity, a Euclidean distance, correlation coefficients or other similarity measure between the embeddings. Further, the machine learning mapping system 106 provides the similarity measure of the relationship between the perturbation classes for display via a graphical user interface of the client device.

As mentioned previously, the machine learning mapping system 106 can use a benchmark model to determine a univariate benchmark measure for the perturbation data. For example, FIG. 4 illustrates determining, utilizing a benchmark model 410, a univariate benchmark measure 412 for a perturbation embedding model 406 and corresponding perturbation data in accordance with one or more embodiments. Specifically, the machine learning mapping system 106 performs an act 404 of receiving a request for a benchmark measure for a perturbation embedding model 406 from a client device 402. Further, the machine learning mapping system 106 identifies perturbation data, such as perturbation experiment unit embeddings 408 corresponding to a plurality of perturbation classes, for the perturbation embedding model 406.

Moreover, the machine learning mapping system 106 utilizes the benchmark model 410 to determine the univariate benchmark measure 412 for the perturbation embedding model 406. Additionally, the machine learning mapping system 106 provides the univariate benchmark measure 412 for the perturbation embedding model 406 for display via a user interface of the client device 402.

As just mentioned, the machine learning mapping system 106 can perform an act 404 of receiving a request for a benchmark measure for a perturbation embedding model 406 from a client device 402. As used herein, the term "benchmark measure," refers to a metric or measure of perturbation data. In particular, the term "benchmark measure" can include a univariate benchmark measure or multivariate benchmark measure. For example, a univariate benchmark measure can include consistency metric and a distance metric. Indeed, the consistency metric can reflect i) the consistency of observed perturbation effects on cells or subjects within a perturbation class, or ii) the signal recovery of a perturbation class relative to a non-perturbation control class. Moreover, the multivariate benchmark measure can include one or more recall metrics. Indeed, a recall metric can reflect the accuracy of predicted relationships (e.g., predicted measures of bioactivity) relative to observed (or known) relationships (e.g., observed measures of bioactivity). In particular, FIG. 4 illustrates the machine learning mapping system 106 receiving a request for a univariate benchmark measure.

Moreover, the term "perturbation embedding model," as used herein, refers to a model that analyzes perturbation data to determine biological relationships between perturbations. In particular, a perturbation embedding model can include a computer-implemented model that generates perturbation-level embeddings for perturbation classes and determines a similarity measure between the perturbation classes. To illustrate, a perturbation embedding model can generate a perturbation-level embedding for each class of a plurality of perturbation classes from perturbation experiment unit embeddings representing measurements of perturbation experiment units in one or more perturbation experiments. Further, the perturbation embedding model can identify a measure of bioactivity between perturbation classes such as by determining a similarity between a first perturbation-level embedding for a first perturbation class and a second perturbation-level embedding for a second perturbation class.

Further, the machine learning mapping system 106 can identify perturbation data, such as perturbation experiment unit embeddings 408 corresponding to a plurality of perturbation classes, for the perturbation embedding model 406. Specifically, the machine learning mapping system 106 can identify the perturbation experiment unit embeddings 408 according to the perturbation class. Thus, the machine learning mapping system 106 utilizes the perturbation experiment unit embeddings 408 of each perturbation class to determine a univariate benchmark measure for the perturbation experiment unit embeddings 408 of each perturbation class. To illustrate, the machine learning mapping system 106 identifies i) the perturbation experiment unit embeddings for a first perturbation class representing a compound perturbation, ii) the perturbation experiment unit embeddings for a second perturbation class representing a second compound perturbation, iii) the perturbation experiment unit embeddings for a third perturbation class representing a gene perturbation, iv) the perturbation experiment unit embeddings for a fourth perturbation class representing an antibody perturbation, etc.

Moreover, the machine learning mapping system 106 can utilize the benchmark model 410 to determine the univariate benchmark measure 412 for the perturbation embedding model 406. The term "benchmark model," as used herein, refers to a model that evaluates perturbation data. In particular, a benchmark model can include a computer-implemented model that determines a benchmark measure. For instance, the benchmark model can determine a univariate benchmark measure and/or a multivariate benchmark measure for a perturbation embedding model.

In one or more embodiments, the machine learning mapping system 106 can utilize the benchmark model 410 to determine a univariate benchmark measure for a perturbation embedding model 406 by determining the consistency and distance metrics. Moreover, the machine learning mapping system 106 can utilize the benchmark model 410 to determine a perturbation embedding model's consistency and distance metrics by determining a consistency perturbation print rate and a distance perturbation print rate, respectively. A perturbation print is a perturbation experiment unit embedding that meet a specified significance threshold of a specified statistical test. The perturbation print rate is the rate of perturbation prints generated by a benchmark model. Further, as part of the process for determining the univariate benchmark measure 412, the machine learning mapping system 106 can determine a cosine similarity, a projection similarity, or an energy distance for the identified perturbation experiment unit embeddings 408 as discussed further below.

For example, the machine learning mapping system 106 utilizes the benchmark model 410 to determine the consistency perturbation print rate by determining a cosine similarity between the perturbation experiment unit embeddings 408 of a perturbation class generated by the perturbation embedding model 406. Indeed, the machine learning mapping system 106 can determine an average cosine similarity as further described with respect to FIG. 7 (i.e., quantifying, using the average cosine similarity between replicates, the consistency of the perturbation profile). Further the machine learning mapping system 106 determines the percentage of perturbation experiment unit embeddings 408 that meet the specified significance threshold of the statistical test. In particular, as described in further detail below with respect to FIG. 7, the machine learning mapping system 106 utilizes the following test statistic:

$$avgsim_g = \frac{1}{n_g n_g} \sum_i^{n_g} \sum_j^{n_g} \frac{\langle x_{g,i}, x_{g,j} \rangle}{\|x_{g,i}\| \|x_{g,j}\|}$$

In this manner, the machine learning mapping system 106 generates the consistency perturbation print rate, which the machine learning mapping system 106 can provide for display via a graphical user interface on the client device 402.

To illustrate, the machine learning mapping system 106 can determine a consistency perturbation print rate for the identified perturbation experiment unit embeddings 408 of the first perturbation class representing a compound perturbation. Indeed, the machine learning mapping system 106 determines the average cosine similarity between the perturbation experiment unit embeddings 408 of the first perturbation class as described. Further, the machine learning mapping system 106 determines the consistency perturbation print rate for the first perturbation class using the test statistic. Moreover, the machine learning mapping system 106 similarly determines a consistency perturbation print rate for each of the identified perturbation classes. Furthermore, the machine learning mapping system 106 can aggregate the perturbation print rates of the perturbation classes (e.g., by averaging the rates or other aggregation methods) to determine an overall consistency perturbation print rate for the perturbation embedding model 406.

In another example, the machine learning mapping system 106 utilizes the benchmark model 410 to determine the distance perturbation print rate by comparing the perturbation experiment unit embeddings 408 of the perturbation class with one or more embeddings of non-perturbation control cells or subjects as generated by the perturbation embedding model. Indeed, the machine learning mapping system 106 determines the distance perturbation print rate by determining an energy distance for the perturbation experiment unit embeddings 408 of the perturbation class. In particular, the machine learning mapping system 106 can determine the energy distance by determining, for each perturbation class, the distance of the distribution of the perturbation experiment unit embeddings 408 to the distribution of the non-perturbation control unit embeddings using one or more tests derived from energy statistics. Indeed, the machine learning mapping system 106 can determine the energy distance via the following energy distance test:

$$\frac{2}{n_1 n_2} \sum_{i=1}^{n_1} \sum_{j=1}^{n_2} \|x_i - y_j\| - \frac{1}{n_1^2} \sum_{i=1}^{n_1} \|x_i - x_j\| - \frac{1}{n_2^2} \|y_i - y_j\|$$

The machine learning mapping system 106 then assesses the statistical significance using a permutation test comparing the distance of the perturbation experiment unit embeddings 408 against null samples (i.e., the non-perturbation control unit embeddings) as further described with respect to FIG. 7. In this manner, the machine learning mapping system 106 generates the distance perturbation print rate, which the machine learning mapping system 106 can provide for display via a graphical user interface on the client device 402.

To illustrate, the machine learning mapping system 106 can determine a distance perturbation print rate for the identified perturbation experiment unit embeddings 408 of the first perturbation class representing a compound perturbation. Indeed, the machine learning mapping system 106 determines the energy distance of the perturbation experiment unit embeddings 408 from non-perturbation control embeddings. For example, the machine learning mapping system 106 determines the distance perturbation print rate for the first perturbation class using the energy distance test and assessing the statistical significance using the permutation test. Moreover, the machine learning mapping system 106 similarly determines a distance perturbation print rate for each of the identified perturbation classes. Furthermore, the machine learning mapping system 106 can aggregate the perturbation print rates of the perturbation classes (e.g., by averaging or other aggregation methods) to determine an overall distance perturbation print rate for the perturbation embedding model 406.

In some embodiments, the machine learning mapping system 106 can determine a projection and/or rejection similarity as part of determining the univariate benchmark measure 412 for the perturbation embedding model 406. For example, the machine learning mapping system 106 determines projection and/or rejection similarities between the perturbation experiment unit embeddings of a perturbation class in the perturbation data associated with the perturbation embedding model 406. Further, the machine learning mapping system 106 utilizes the projection or rejection similarities to determine perturbation print rates for the perturbation embedding model 406 using the benchmark model 410. For example, the machine learning mapping system 106 utilizes the projection and/or rejection similarities in a similar manner as the cosine similarities are used as described above.

In one or more embodiments, the machine learning mapping system 106 determines the univariate benchmark measure 412 by identifying whether a perturbation class has a perturbation print/fingerprint (e.g., a phenoprint, a transcriptoprint, etc.). In these or other embodiments, the machine learning mapping system 106 identifies that a perturbation class has a perturbation print by determining that the perturbation class satisfies a threshold level of similarity, consistency, reliability, or accuracy (e.g., whether the cross-validated angle (CV-angle) p-value of the perturbation class meets a threshold value, such as 0.01).

For example, using the benchmark model 410, the machine learning mapping system 106 calculates the CV-angle for each replicate of the perturbation class. As used herein, the term "replicate" refers to a duplicate, repeat, or reproduction (e.g., of an embedding). For example, a replicate can include an aggregation of perturbation experiment unit embeddings within the same perturbation class. Further, the machine learning mapping system 106 can aggregate the perturbation experiment unit embeddings in various ways to generate the replicates. For example, the machine learning mapping system 106 can aggregate the perturbation experiment unit embeddings according to the well of a slide (for perturbation experiments using slides) to generate well-level replicates. In some implementations, the machine learning mapping system 106 can aggregate the perturbation experiment unit embeddings according to CRISPR guides targeting a specific gene (e.g., for gene perturbations) to generate guide-level replicates.

As mentioned, the machine learning mapping system 106 identifies the perturbation print for a perturbation class by calculating the CV-angle for the perturbation class. For example, the machine learning mapping system 106 determines a CV-angle for each replicate with respect to the other replicates of the same perturbation class. As used herein, the CV-angle refers to the angle between the vector representation of a replicate and the average vector representation of the other replicates of the same perturbation class. Further, the machine learning mapping system 106 averages the CV-angle of all the replicates of a perturbation class to determine the mean-CV-angle for use as a test statistic for that perturbation class.

Further, in some implementations, the machine learning mapping system 106 generates a mean-CV-angle p-value for the perturbation class using the mean-CV-angle. For example, the machine learning mapping system 106 generates the mean-CV-angle p-value by comparing the mean-CV-angle of a given perturbation class to a null distribution calculated from a variety of different perturbation classes, controlling for perturbation class (and controlling for well location for perturbations performed on well plates). In these or other embodiments, this mean-CV-angle p-value represents the proportion of mean-CV-angles in the null distribution that are smaller than the mean-CV-angle for the perturbation class of interest. In one or more embodiments, the null distribution contains 10,0000 random samples (e.g., perturbation experiment unit embeddings of the various perturbation classes). Accordingly, in these or other embodiments, the machine learning mapping system 106 can reliably assess a mean-CV-angle p-value of 0.0001.

Moreover, the machine learning mapping system 106 can also generate z-scores using the mean-CV-angles when identifying perturbation prints. For example, the machine learning mapping system 106 converts the mean-CV-angle statistics to z-scores by calculating the mean and standard deviation of the null and standardizing to these values. In some embodiments, such as where the perturbation class has values across perturbation experiments, the machine learning mapping system 106 can use a median of the mean-CV-angle p-values across the perturbation experiments. In other examples, the machine learning mapping system 106 can use a mean, or other measure, of the mean-CV-angle p-values across perturbation experiments.

In some implementations, such as those with guide-level replicates (e.g., gene perturbations), the machine learning mapping system 106 generates the null distribution from guide-level replicates targeting different genes than the CRISPR guides of the perturbation class of interest. Further, in these or other embodiments, the machine learning mapping system 106 can utilize multiple CRISPR guides (e.g., 4 or more guides) to target a single gene. These multiple guides are also referred to herein as a cardinality. In these or other embodiments, the machine learning mapping system 106 generates different null distributions for each cardinality. Moreover, in one or more embodiments, the machine learning mapping system 106 can identify whether a perturbation class has a perturbation print by comparison with a null distribution as described in U.S. Pat. No. 10,146,914, issued Dec. 4, 2018, entitled SYSTEMS AND METHODS FOR EVALUATING WHETHER PERTURBATIONS DISCRIMINATE AN ON TARGET EFFECT, the contents of which are herein incorporated by reference in their entirety. Additionally, the machine learning mapping system 106 can identify perturbation print rates separately for expressed and non-expressed genes using RNA-seq data and a z-score and for Fragments Per Kilobase of transcript per Million mapped reads (zFPKM) cutoff of −3.0.Additionally, the machine learning mapping system 106 can provide the univariate benchmark measure 412 for the perturbation embedding model 406 for display via a user interface of the client device 402. For example, the machine learning mapping system 106 provides the univariate benchmark measure 412 for the perturbation embedding model 406 including the consistency and/or distance metrics (e.g., the consistency and/or distance perturbation print rates determined by the machine learning mapping system 106). Indeed, the machine learning mapping system 106 provides, for display on the client device 402, the univariate benchmark measure 412 for the benchmark model 410 including the consistency and/or distance metrics for each of the identified perturbation classes, including an aggregate consistency metric and/or aggregate distance metrics, or including both. Further detail regarding the display of the univariate benchmark measure 412 on the client device 402 via a graphical user interface will be discussed with respect to FIG. 6.

As mentioned previously, the machine learning mapping system 106 can determine a multivariate benchmark measure for the perturbation data using the benchmark model. For example, FIG. 5 illustrates determining, utilizing a benchmark model 510, a multivariate benchmark measure 520 for a perturbation embedding model 506 and corresponding perturbation data in accordance with one or more embodiments. Specifically, the machine learning mapping system 106 performs an act 504 of receiving a request for a benchmark measure for a perturbation embedding model 506 from a client device 502. Further, the machine learning mapping system 106 identifies perturbation data, such as similarity measures 508 between perturbation classes, for the perturbation embedding model 506. Moreover, the machine learning mapping system 106 utilizes the benchmark model 510 to determine the multivariate benchmark measure 520 for the perturbation embedding model 506. Furthermore, the machine learning mapping system 106 determines the multivariate benchmark measure 520 by comparing a predicted measure of bioactivity 514 with an observed measure of bioactivity 516. Additionally, the machine learning mapping system 106 provides the multivariate benchmark measure 520 for the perturbation embedding model 506 for display via a user interface of the client device 502.

As noted, the machine learning mapping system 106 can perform an act 504 of receiving a request for a benchmark measure for a perturbation embedding model 506 from a client device 502. Moreover, the machine learning mapping system 106 can receive perturbation data for the perturbation embedding model 506 with the request. For instance, the machine learning mapping system 106 receives perturbation data for the perturbation embedding model 506 such as perturbation experiment unit embeddings, perturbation-level aggregated experiment unit embeddings and similarity measures 508 between perturbation-level aggregated embeddings. As used herein, the term "perturbation-level aggregated embedding" refers to a composite embedding of perturbation experiment unit embeddings. For example, a perturbation embedding model 506 can include perturbation experiment unit embeddings which are aggregated into a single embedding representing all the perturbation experiment unit embeddings of a single perturbation class. Further, the term "perturbation-level aggregated embedding" refers to an aggregate embedding using an aggregation method of the perturbation embedding model 506. Thus, the term "perturbation-level aggregated embedding" refers to a generically aggregated embedding as opposed to the term "perturbation-level embedding," which is an embedding aggregated according to an aggregation model as discussed with regard to FIG. 3B. Indeed, a perturbation-level aggregated embedding can include a perturbation-level embedding or an embedding aggregated via some other method of the perturbation embedding model 506. In particular, FIG. 5 illustrates the machine learning mapping system 106 receiving a request for a multivariate benchmark measure 520.

Further, the machine learning mapping system 106 can identify perturbation data, such as similarity measures 508 between perturbation classes, for the perturbation embedding model 506. Indeed, the machine learning mapping system 106 identifies a similarity measure 508 between the perturbation-level aggregated embedding for one perturbation class and the perturbation-level aggregated embedding for another perturbation class. To illustrate, the machine learning mapping system 106 identifies in the perturbation data associated with the perturbation embedding model 506 a similarity measure between a first aggregated perturbation-level aggregated embedding for a first perturbation class representing a first gene perturbation and a second perturbation-level aggregated embedding for a second perturbation class representing a second gene perturbation. Further, the machine learning mapping system 106 can identify all of the similarity measures associated with the perturbation embedding model 506 regardless of the underlying perturbations included therein. Indeed, the similarity measures can be between data for any type of perturbation described previously such as compound perturbations, protein perturbations, antibody perturbations, gene perturbations, virus perturbations, in vivo perturbations, etc.

Moreover, the machine learning mapping system 106 can utilize the benchmark model 510 to determine the multivariate benchmark measure 520 for the perturbation embedding model 506. Indeed, the machine learning mapping system 106 determines the multivariate benchmark measure 520 by comparing bioactivity 512 of a predicted measure of bioactivity 514 with an observed measure of bioactivity 516. As used herein, the term "measure of bioactivity" refers to an indication of a biological relationship, expression, or activity. Thus, for instance, a measure of bioactivity can indicate an indication, metric, or measure of a relationship between a stimulus and a corresponding biological result. To illustrate, a measure of bioactivity can indicate a perturbation that corresponds to a biological result. In some implementations, the machine learning mapping system 106 generates a measure of bioactivity as a similarity between perturbation classes. Specifically, the term "measure of bioactivity" can include a similarity measure between perturbation-level aggregated embeddings representing different classes. To illustrate, a measure of bioactivity includes a cosine similarity or other similarity measure between a first perturbation-level aggregated embedding representing a first perturbation class and a second perturbation-level aggregated embedding representing a second perturbation class. Further, a predicted measure of bioactivity can be a measure of bioactivity predicted by a perturbation embedding model.

An observed measure of bioactivity can be a previously identified measure of bioactivity (e.g., representing a known biological relationship, such as a relationship identified in or received from an external database). Such external databases can include protein-protein interaction databases (e.g., Reactome), pathway interaction databases (e.g., Signaling Network Open Resource also referred to herein as SIGNOR), and protein complex databases (e.g., Comprehensive ResoUrce of Mammalian protein complexes also referred to herein as CORUM).

As mentioned, the machine learning mapping system 106 can compare a predicted measure of bioactivity 514 with an observed measure of bioactivity 516 to determine the multivariate benchmark measure 520 as illustrated in FIG. 5. For example, the machine learning mapping system 106 compares the predicted measure of bioactivity 514 identified in the perturbation data for the perturbation embedding model 506 to an observed measure of bioactivity from external database data 518. To illustrate, the machine learning mapping system 106 compares the identified similarity measure between the first perturbation-level aggregated embedding for the first perturbation class representing a first gene perturbation and the second perturbation-level aggregated embedding for the second perturbation class representing a second gene perturbation with the relationship information for the same two genes in the external database data 518.

To illustrate, the machine learning mapping system 106 can compare various predicted measures of bioactivity 514 with corresponding observed measures of bioactivity 516. Indeed, the machine learning mapping system 106 compares the predicted measure of bioactivity between Genes A, B, and C, the predicted measure of bioactivity between Gene C and D, and the predicted measure of bioactivity between Genes D, E, and F (as illustrated in the heatmap of the multivariate benchmark measure 520 of FIG. 5) with observed measures of bioactivity in the external database data 518 (as illustrated in the diagram of the multivariate benchmark measure 520 of FIG. 5). In this example, the darker shading of the cells of the heatmap represents a high similarity in the bioactivity of the corresponding genes. For example, the heatmap demonstrates that the perturbation embedding model 506 identified a strong similarity between genes A, B, and C, between genes D, E, and F, and between genes G and H. Further, the machine learning mapping system 106 compares these measures of bioactivity between genes with the observed measures of bioactivity 516 between these genes from the external database data 518. Indeed, the illustration of the multivariate benchmark measure 520 includes an overlay of the observed measures of bioactivity 516 on the heatmap containing the similarity measures determined by the perturbation embedding model 506. As illustrated the perturbation embedding model 506 accurately determined the known relationship between genes A, B, and C as well as the known relationship between genes D, E, and F as illustrated by the dashed line overlay on the heatmap. The perturbation embedding model 506, however, failed to determine the known relationship between Genes C and D as illustrated by the solid line overlay on the heatmap. Accordingly, by generating the multivariate benchmark measure 520, the machine learning mapping system 106 provides a measure of the ability of the perturbation embedding model 506 to accurately determine new relationships, such as the newly determined relationship between genes G and H as illustrated by the dotted line overlay.

In some embodiments, the machine learning mapping system 106 utilizes a projection and/or rejection similarity as part of determining the multivariate benchmark measure 520 for the perturbation embedding model 506. For example, the machine learning mapping system 106 identifies, in the perturbation data of the perturbation embedding model 506, projection similarities between the perturbation-level aggregated embeddings of the perturbation classes generated by the perturbation embedding model 506. In these or other embodiments, these projection similarities are one method of representing the predicted measure of bioactivity 514. Further, the machine learning mapping system 106 utilizes the benchmark model 510 to compare the predicted measure of bioactivity 514 with an observed measure of bioactivity 516 as discussed above.

Figure 6:
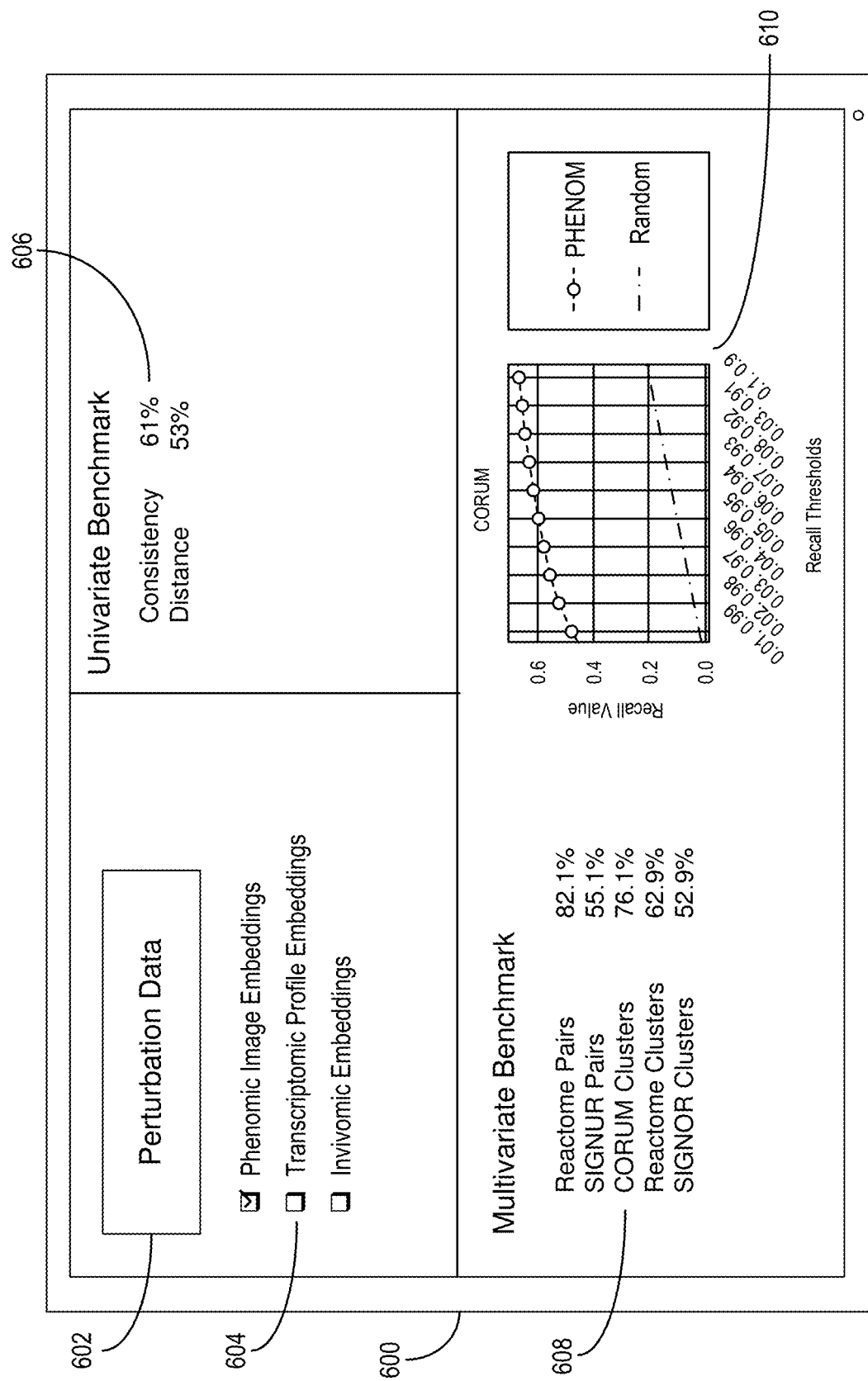
FIG. 6 illustrates an exemplary graphical user interface on a client device displaying perturbation data elements and benchmark measures in accordance with one or more embodiments.

Additionally, the machine learning mapping system 106 can provide the multivariate benchmark measure 520 for the perturbation embedding model 506 for display via a user interface of the client device 502. Moreover, the machine learning mapping system 106 can generate various representations of the multivariate benchmark measure 520 for display via a user interface of the client device 502. For example, the machine learning mapping system 106 utilizes the benchmark model 510 to determine a multivariate benchmark measure 520 including one or more recall metrics. As used herein, the term "recall metric" refers to the percentage of known relationships (e.g., gene pairs, gene clusters, or other relationships between perturbation classes) that the benchmark model 510 identifies when determining the predicted measure of bioactivity 514. Indeed, the machine learning mapping system 106 can generate the recall metric as a percentage as shown in FIG. 6.

As mentioned above, the machine learning mapping system 106 can provide a univariate benchmark measure and/or a multivariate benchmark measure for display via a user interface of a client device. For example, FIG. 6 illustrates an exemplary graphical user interface 600 on a client device displaying perturbation data elements and benchmark measures in accordance with one or more embodiments. Specifically, the machine learning mapping system 106 generates the graphical user interface 600 in response to receiving a request for a benchmark measure for a perturbation embedding model and perturbation data associated with the model via a perturbation data input element 602. Optionally, the machine learning mapping system 106 can generate the graphical user interface 600 to include a perturbation data designation element 604 for receiving a perturbation data type designation. Moreover, the machine learning mapping system 106 provides, for display on a client device via the graphical user interface 600, a univariate benchmark measure 606 and/or a multivariate benchmark measure 608.

As just mentioned, the machine learning mapping system 106 can generate the graphical user interface 600 for receiving a request for a benchmark measure for a perturbation embedding model and perturbation data associated with the model via a perturbation data input element 602. For example, the machine learning mapping system 106 generates the graphical user interface 600 for display on a client device. Further, the machine learning mapping system 106 receives, from the client device, a request for a benchmark measure for a perturbation embedding model and the perturbation data associated with the perturbation embedding model via the perturbation data input element 602. In some embodiments, the machine learning mapping system 106 also generates the graphical user interface 600 to include a perturbation data designation element 604. In these or other embodiments, the machine learning mapping system 106 receives a designation of the type of perturbation data included with the model (e.g., phenomic image embeddings, transcriptomic profile embeddings, invivomic embeddings, etc.).

To illustrate, the machine learning mapping system 106 can receive the request and perturbation data associated with a perturbation embedding model via the perturbation data input element 602 along with a perturbation data designation via the perturbation data designation element 604. For example, as illustrated in FIG. 6, the machine learning mapping system 106 receives perturbation data comprising phenomic image embeddings generated from phenomic image perturbation data. Additionally, in some embodiments the machine learning mapping system 106 receives data having multiple types of perturbation data. In these or other embodiments, the machine learning mapping system 106 receives a perturbation data designation indicating multiple types of perturbation data. Furthermore, in some implementations, the machine learning mapping system 106 determines the type/s of perturbation data without receiving a data designation.

Moreover, the machine learning mapping system 106 can determine a univariate and/or a multivariate benchmark measure for the perturbation embedding model in response to receiving the request for the benchmark measure for the perturbation embedding model and corresponding perturbation data. For example, in response to receiving the request for the benchmark measure/s and the perturbation data, the machine learning mapping system 106 identifies the perturbation data. Indeed, the machine learning mapping system 106 identifies the perturbation experiment unit embeddings generated by the perturbation embedding model, the perturbation-level aggregated embeddings for each perturbation class, the similarity measures between perturbation-level aggregated embeddings generated by the perturbation embedding model, etc. Further, the machine learning mapping system 106 determines the univariate benchmark measure and/or the multivariate benchmark measure for the perturbation embedding model utilizing a benchmark model as discussed with respect to FIGS. 4 and 5.

Moreover, the machine learning mapping system 106 can provide, for display via the graphical user interface 600 of the client device, a univariate benchmark measure 606 and/or a multivariate benchmark measure 608. For example, the machine learning mapping system 106 provides the univariate benchmark measure 606, including consistency and distance metrics, for the perturbation embedding model for display in the graphical user interface 600 as illustrated in FIG. 6. To illustrate, the machine learning mapping system 106 receives perturbation data of a perturbation embedding model including transcriptomic profile embeddings. The machine learning mapping system 106 identifies the perturbation experiment unit embeddings for each perturbation class represented in the perturbation data. The machine learning mapping system 106 then utilizes the benchmark model to determine the univariate benchmark measure 606, including consistency and distance metrics, for the perturbation embedding model as discussed above with respect to FIG. 4. Further, the machine learning mapping system 106 provides the univariate benchmark measure 606, in numerical form, to the graphical user interface 600 as shown in FIG. 6.

In another example, the machine learning mapping system 106 can provide the multivariate benchmark measure 608, including one or more recall metrics for specific biological relationships, for the perturbation embedding model for display in the graphical user interface 600 as illustrated in FIG. 6. To illustrate, the machine learning mapping system 106 receives perturbation data of a perturbation embedding model including transcriptomic profile embeddings. The machine learning mapping system 106 identifies the similarity measures between the perturbation-level aggregated embeddings for each perturbation class represented in the perturbation data to determine one or more predicted measures of bioactivity and further determines observed measures of bioactivity from external database data as discussed with respect to FIG. 5. The machine learning mapping system 106 then utilizes the benchmark model to determine the multivariate benchmark measure 608, including the one or more recall metrics. Further, the machine learning mapping system 106 provides the multivariate benchmark measure 608, in numerical form, to the graphical user interface 600 as shown in FIG. 6.

Moreover, the machine learning mapping system 106 can provide the univariate benchmark measure 606 or the multivariate benchmark measure 608 for display in the graphical user interface 600 via a variety of different representations. For example, the machine learning mapping system 106 can provide the benchmark measures via a numerical representation as shown in FIG. 6, via one or more graphical representations, via one or more tables, etc. Indeed, as illustrated in FIG. 6, the machine learning mapping system 106 includes a graph 610 indicating recall values of an embedding model (labeled PHENOM) and corresponding embeddings according to varying thresholds. The machine learning mapping system 106 can also generate the graph 610 to include recall values for multiple different embedding models. Thus, the graphical user interface 600 allows for selection of multiple models (and multiple embeddings) and generating comparisons of multiple models in a single user interface.

FIGS. 7-16 illustrate experimental results from, and further detail regarding, the implementation of the methods and systems discussed above with respect to FIGS. 1-6. As mentioned, the machine learning mapping system 106 can utilize genomic technologies and high-throughput screening capabilities to build maps of biology through unbiased, large-scale profiling of genetic perturbations. These maps have massive potential to uncover novel biology and accelerate drug discovery processes. For example, the machine learning mapping system 106 can utilize CRISPR interference (CRISPRi) or CRISPR-mediated gene knockouts to build genome-wide perturbation maps using single cell RNA-seq or cellular imaging as readouts. Moreover, the machine learning mapping system 106 can utilize a systematic framework for constructing and evaluating such maps by suggesting a shared schema and benchmarking criteria, which will lead to more stable, transferable, and useful analyses of future maps of biology.

This disclosure utilizes the term "perturbation unit" synonymously with "perturbation experiment unit" to reflect an experimental entity that is measured in a map (e.g., the smallest experimental entity) as discussed above.

As illustrated in FIG. 2, the machine learning mapping system 106 can utilize a variety of post-experimental process steps to build a map (which relates perturbations to one another in a meaningful way) from these raw assay data. In one or more implementations, the machine learning mapping system 106 divides these transformations into five categories (referred to herein as the "EFAAR pipeline"). EFAAR steps may take place in a different order, multiple times (e.g., perturbation units may be filtered pre- and post-embedding), or potentially in a single end-to-end process.

Embedding assay data from each perturbation unit to generate a vector representation
Filtering perturbation units that do not pass quality criteria
Aligning different batches of perturbation units
Aggregating units representing each perturbation (e.g., a gene)
Relating different perturbations to each other (e.g., identifying gene relationships)

Embedding perturbation units: This step is aimed at creating a vector representation of the experimental screening results. Intermediate layers of neural networks are commonly used to generate embeddings for unstructured data (e.g., cell images). Linear dimensionality reduction methods like k-means or principal component analysis (PCA) are common for structured data such as transcriptomic profiles, however non-linear dimensionality reduction techniques based on neural networks have been found to be effective as well.

Filtering perturbation units or perturbations: In any experimental screening process, some perturbation units will not satisfy pre-defined quality criteria and need to be filtered out. This filtering can occur before or after embeddings are generated, or before the relationships are generated. Examples include wells with too high or too low pixel intensity in a cellular imaging screen or perturbation units that are not distinguishable from the controls in terms of their readout or embeddings.

Aligning batches: A batch effect is a systematic effect shared by all observations obtained under similar experimental conditions (e.g., microscopy acquisition artifacts, donor batch, incubation times) that potentially confound the interpretation of desired biological signal from the readouts. A baseline approach for aligning perturbation units is to use control units in each batch to center and scale features in each set. Another linear method aligning not only the first order statistics but also the covariance structures is TVN (typical variation normalization). Non-linear methods based on nearest neighbor matching or on conditional variational autoencoders, have been successful for the alignment of single cell transcriptomic data.

Aggregating perturbation units: There are typically multiple technical or biological replicates representing each perturbation in a given map, e.g., the same perturbation may be applied to dozens of wells or hundreds of cells. Aggregation of these replicates is significant for a robust final representation of a perturbation. For example, the machine learning mapping system 106 can utilize coordinate-wise mean and/or median aggregation. The machine learning mapping system 106 can also utilize methods like the Tukey median to reduce the impact of outliers on the final representation.

Relating perturbations: The machine learning mapping system 106 can identify relationships between biological entities (e.g., gene-gene interactions arising from protein complexes or signaling pathways) utilizing maps built based on genetic perturbations. The machine learning mapping system 106 can compute distances (e.g., Euclidean or cosine) between aggregated perturbation representations as a proxy for relationships, where smaller distance means a stronger relationship. These distances, in turn, can also be used to visualize the global structure of perturbations through further dimensionality reduction techniques such as uniform manifold approximation (UMAP) or minimum-distortion embedding (MDE).

Benchmarking can be done to evaluate the ability of an EFAAR pipeline to recover signal on individual perturbations (utilizing the perturbation replicates after alignment) or on its ability to recover relationships (utilizing the relationships between aggregate representations). Moreover, the machine learning mapping system 106 can intelligently determine and display these benchmarks via user interfaces of client devices to improve accuracy and analysis of these systems. For example, the machine learning mapping system 106 can utilize univariate and multivariate benchmarks. Furthermore, researchers have conducted experiments on two orthogonal datasets.

Joseph M Replogle, Reuben A Saunders, Angela N Pogson, Jeffrey A Hussmann, Alexander Lenail, Alina Guna, Lauren Mascibroda, Eric J Wagner, Karen Adelman, Gila Lithwick-Yanai, et al. in Mapping information-rich genotype-phenotype landscapes with genome-scale perturb-seq (hereinafter Replogle), perturb approximately 10,000 expressed genes in K562 cells using CRISPRi and measure single-cell RNA-seq readout to generate a transcriptomic map. Another dataset from Recursion contains a proprietary collection of imaging data in which CRISPR knockout technology was used to target approximately 17,000 genes in primary HUVEC cells.

The machine learning mapping system 106 can implement various embodiments of the methods for embedding, filtering, aligning, aggregating, and relating the transcriptomic perturbation data to generate transcriptomic maps. For example, in one or more implementations, the machine learning mapping system 106 downloaded pre-filtered single-cell gene expression (e.g., for K562 cells from gwps.wi.mit.edu). In one or more experimental implementations, the machine learning mapping system 106 used either the top 100 principal components from PCA or 128 latent dimensions from scVI (singlecell variational inference), a conditional variational auto-encoder providing both embedding and alignment. Below are the EFAAR steps specifying choices of the different pipelines used by an experimental implementation of the machine learning mapping system 106 to build the transcriptomic maps and generate benchmarks.

· Align & Embed: (Choice 1) Compute the mean and standard deviation of all non-targeting controls per batch and use those to z-score all cells in the same batch and apply PCA and retain top 100 principal components. (Choice 2) Obtain a vector representation through sc VI using a network that has two hidden layers with 256 nodes and 128 latent dimensions.

Align: Compute the mean over all non-targeting controls in the PCA space and subtract this mean vector from all cells.

Aggregate: Compute the mean vector across cells for each perturbation.

Filter: (Choice 1) Keep all genes. (Choice 2) Exclude genes without transcriptoprint.

Relate: Compare perturbations using cosine similarity.

Similarly, the machine learning mapping system 106 can implement various embodiments of the methods for embedding, filtering, aligning, aggregating, and relating the phenomic imaging perturbation data to generate phenomic maps. The pipeline starts with six-channel Recursion cell painting images of wells. Researchers generated embeddings by extracting activation values from an intermediate layer of a weakly supervised convolutional neural network (CNN) and apply two post-embedding alignment methods: Centerscale (per-batch standardization) and TVN. Below are the EFAAR steps specifying choices of the different pipelines used by one or more embodiments of the machine learning mapping system 106 to build a phenomic maps benchmarked (as described in greater detail below).

Embed & Align: Pass images through a pre-trained CNN and store the activations from an intermediate layer to obtain a fixed-length vector representation of the image. This model was trained to be partially resilient to batch effects.

Filter: Apply additional proprietary filters to remove outlier image embeddings.
Align: (Choice 1) Batch-correct by center-scaling (z-scale) per batch using experimental controls included in each batch. (Choice 2) Apply TVN [8] using experimental controls from all batches.
Aggregate: Compute the mean vector over each perturbation.
Filter: (Choice 1) Keep all genes. (Choice 2) Exclude genes without phenoprint.
Relate: Compare perturbations using cosine similarity.

As discussed above with respect to FIG. 4, the machine learning mapping system 106 can determine a univariate benchmark measures (also referred to herein as univariate benchmarks) for a perturbation embedding model by determining perturbation print rates. The machine learning mapping system 106 can utilize univariate benchmarks to assess the reproducibility and robustness of the representations of individual perturbations in a map. For instance, in some implementations, the machine learning mapping system 106 utilizes: (1) consistency of the perturbation profile across replicates quantified with the average cosine similarity between replicates, and/or (2) magnitude of the perturbation effect quantified with energy distance.

For example, the machine learning mapping system 106 can determine the consistency of the perturbation profile across replicates for a genetic perturbation g, with access to a total number of $n_g$ query perturbation units. For each perturbation unit $i=1, \ldots, n_g$, the machine learning mapping system 106 generates (or accesses) an embedding vector $x_{g,i}$. Moreover, each perturbation unit is associated with a batch $b_{g,i} \in \{1, \ldots, B\}$. Let $g_b$ denote all perturbation units if g in batch b, and let $|g_b|=n_{g,b}$. Thus, $g=U_{b=1}^{B} g_b$, and $|g|=n_g$.

As the test statistic, the machine learning mapping system 106 can use avgsim, defined as the mean of the cosine similarity between each perturbation unit's profile and the profiles of all other perturbationI units for g (i.e., in all batches). Formally (Eq. 1), $$avgsim_g = \frac{1}{n_g n_g} \sum_i^{n_g} \sum_j^{n_g} \frac{\langle x_{g,i}, x_{g,j} \rangle}{\|x_{g,i}\|\|x_{g,j}\|}.$$

Parametric tests are not preferred for univariate metrics because the underlying population of distances do not typically follow a well-defined probability distribution. Consequently, in one or more implementations the machine learning mapping system 106 assesses statistical significance of a gene g's perturbation profile using a non-parametric test on K empirical null perturbation samples that are generated considering the batch distribution of the $n_g$ cells to $b \in \{1, \ldots, B\}$. This is utilized because there could be batch effects remaining even after batch correction. The kth null sample for g, denoted as $g'_k$, is generated as follows. From each batch b with $n_{g,b}>0$, draw $n_{g,b}$ cells uniformly at random, denoted by $g'_{k,b}$. Thus, $g'_k=U_{b=1}^{B} g'_{k,b}$. The machine learning mapping system 106 then computes avgsim $g'_k$ for $k=1, \ldots, K$ (K=1000) as above and assigns a p-value to perturbation g by (Eq. 2)

$$p_g = \frac{\max\{\#\{avgsim_{g'_k} \leq avgsim_g\}, 1\}}{K}.$$

For the transcriptomic data, the machine learning mapping system 106 can use cells as query perturbation units, and for the phenomic data, the machine learning mapping system 106 can use CRISPR guides as query perturbation units. Replacing avgsim with a leave-one-out average cosine similarity (loosim) can allow for outlier handling (e.g., for the phenomic data). Below (Eq. 3) is how the machine learning mapping system 106 determines loosim in one or more embodiments.

$$loosim_g = \frac{1}{n_g} \sum_i^{n_g} \frac{\langle x_{g,i}, \overline{x}_{g,i'} \rangle}{\|x_{g,i}\|\|x_{g,i'}\|}.$$

where $\overline{x}_{g,i'}$ represents the average representation over all but the ith unit (Eq. 4):

$$\overline{x}_{g,i'} = \frac{1}{n_g - 1} \sum_{j \neq i} x_{g,j}.$$

Moreover, the machine learning mapping system 106 can determine the energy distance of the perturbation profile across replicates of a perturbation class. The energy distance measures how distanced the replicate units of a perturbation are from the controls, essentially measuring the effect size of the perturbation in a high-dimensional space. For each query perturbation, the machine learning mapping system 106 can compute the distance of the replicate perturbation units' distribution to the control units' distribution using tests derived from energy statistics. Assuming access to two sets of embeddings $x_1, \ldots, x_{n_1}$ (representing query perturbation units) and $y_1, \ldots, y_{n_2}$ (representing control units), the energy distance is defined as (Eq. 5)

$$\frac{2}{n_1 n_2} \sum_{i=1}^{n_1} \sum_{j=1}^{n_2} \|x_i - y_j\| - \frac{1}{n_1^2} \sum_{i=1}^{n_1} \|x_i - x_j\| - \frac{1}{n_2^2} \|y_i - y_j\|.$$

This distance will be zero when the distributions are identical, and positive between non-identical distributions. The machine learning mapping system 106 assesses the statistical significance using a permutation test comparing the distance of the query perturbation against a large number of null samples generated through shuffling the labels of the query perturbation and control units. In one example implementation, the machine learning mapping system 106 utilized 1000 null samples and computed the p-value in a similar fashion to Eq. (2).

Similar to the perturbation consistency computation, in one or more example implementations the machine learning mapping system 106 utilizes, as perturbation units, cells for the transcriptomic data, and CRISPR guides for the phenomic data. For transcriptomic data, to construct the null distribution to compare against each perturbation, in one or more example implementations the machine learning mapping system 106 randomly sub-sampled 5% of all perturbation units that received the non-targeting control in any of the batches containing the query perturbation. Subsampling can assist in reducing computation time.

Figure 9:
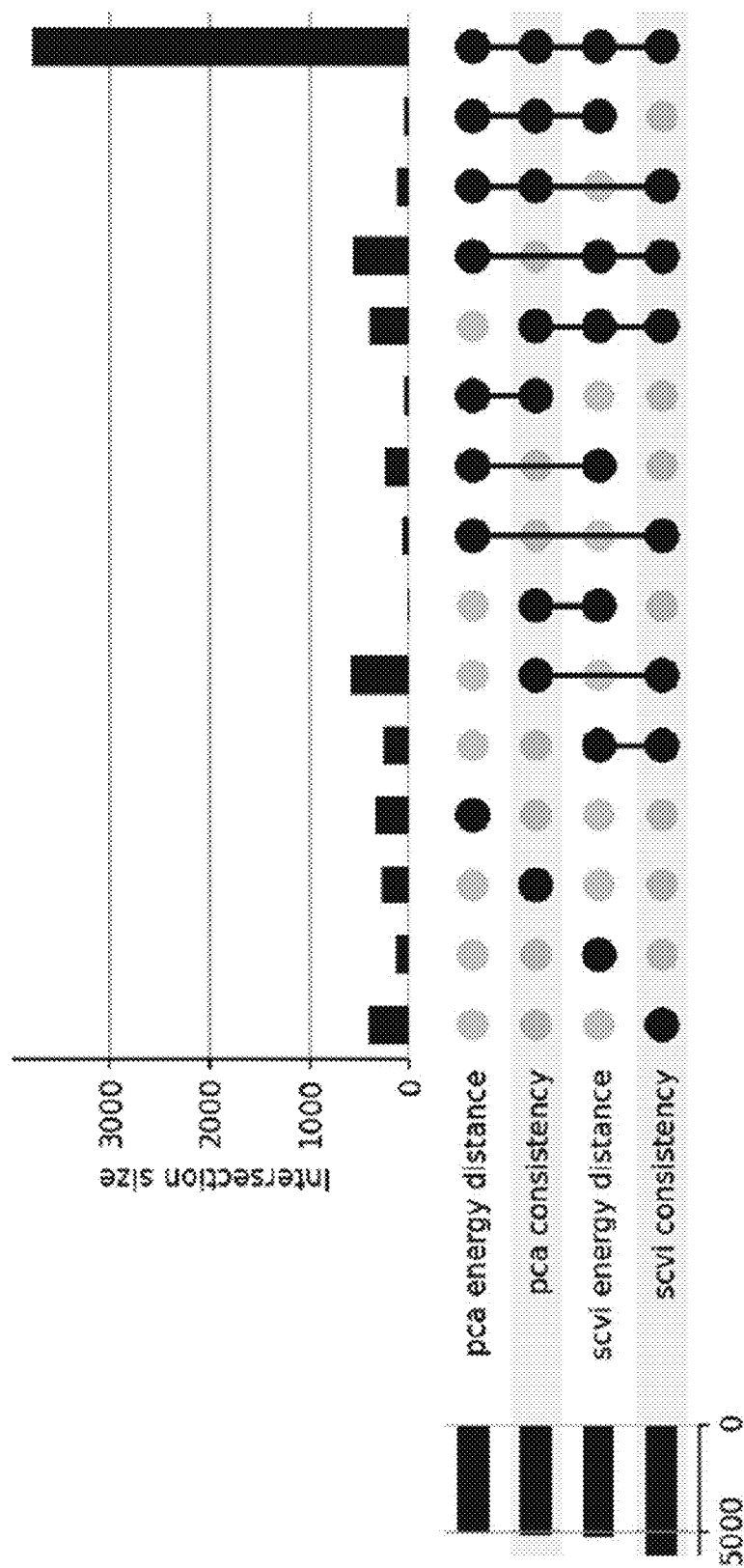
FIG. 9 illustrates a plot of the intersection of transcriptoprints from two embedding/alignment choices and two univariate benchmark metrics in accordance with one or more embodiments.

For both of these metrics, results of statistical significance tests can be found below. Below, representations of perturbations that pass a certain significance threshold from the associated statistical tests are referred to as "phenoprints" in phenomic maps, "transcriptoprints" in transcriptomic maps, or "perturbation prints" to cover both cases. Rates of perturbation print identification can be compared between different map processing pipelines (EFAAR parameter choices) and stratified by global annotations like gene expression or functional gene groups. Researchers measured the perturbation print rates with above univariate metrics in Replogle data and Recursion data. For Replogle data, scVI-based EFAAR pipeline outperformed PCA-based one in terms of transcriptoprint rate with either metric (see FIG. 7), identifying slightly more genes. 38% of all targeted genes were identified as significant across both methods and metrics (see FIG. 9), while 29% of perturbed genes were not detected by any tested condition. In particular, FIG. 9 illustrates an UpSet plot of the intersection of transcriptoprints from two EFAAR embedding/alignment choices and two univariate benchmark metrics. Bar height reflects the number of genes with transcriptoprints (p-value <0.01) in the group(s) represented by the solid circles below. Bar plot on the left shows the totals for each EFAAR choice and univariate metric in accordance with one or more embodiments.

For Recursion data, researchers determined results relative to the output of the first step describing phenomic maps above, referred to as CNN-BC (convolutional neural network with batch correction). While TVN leads to a large improvement over CNN-BC in both consistency and distance, Centerscale result is only slightly better than CNN-BC (see FIG. 7). This may come as a result of the batch effect correction component of CNN-BC. To test this hypothesis, researchers assessed, as a baseline, a different embedding model lacking the batch effect resiliency component, referred to as CNN-noBC. Applying Centerscale on top of CNN-noBC improved performance by 583% in consistency and by 493% in distance (see FIG. 8).

Furthermore, the machine learning mapping system 106 can determine a multivariate benchmark for a perturbation embedding model, for example, by utilizing a map of biology to discover novel, biologically-relevant relationships between genes or between a gene and a small molecule (e.g., a drug candidate). In one or more embodiments, the machine learning mapping system 106 utilizes gene-based benchmark sources: pairwise relationships and/or gene clusters. For instance, (with regard to the first type) the machine learning mapping system 106 can utilize pairs that directly interact in a signaling pathway or a small protein interaction network. Similarly (with regard to the second type), the machine learning mapping system 106 can utilize clusters that represent all genes involved in a pathway, biological process, or protein complex, which provide higher-level information for biological processes or pathways.

The machine learning mapping system 106 can utilize pairwise relationship recapitulation and/or cluster identification results. The machine learning mapping system 106 can, before the Relate step, remove perturbations that do not have a perturbation print. For pairwise relationships, the machine learning mapping system 106 can utilize a variety of data sources. For example, consider two publicly-available sources: Reactome protein-protein interactions from protein complexes with at most four proteins, and Signaling Network Open Resource (SIGNOR) pathway interactions. Similarly, for cluster identification metrics the machine learning mapping system 106 can utilize a variety of data searchers. To illustrate, consider three publicly-available sources: Reactome (gene sets from MSigDB C2 collection), SIGNOR pathways, and Comprehensive ResoUrce of Mammalian (CORUM) protein complexes.

For both pairwise and cluster metrics, in one or more example embodiments, the machine learning mapping system 106 reports the recall of annotated pairs within the most extreme 10% of pairwise relationships (considering 5% from both tails of the pairwise distance distribution since negative relationships can indicate a negative signaling between genes). For cluster metrics the machine learning mapping system 106 determines a recall value per cluster and then averages the per-cluster values to get the final metric.

To assess how well a map embedding recapitulates known biology, in one or more implementations, the machine learning mapping system 106 calculates recall measures on known pairwise relationships and known clusters as follows. For pairwise relationships, the machine learning mapping system 106 calculates pairwise cosine similarities between the aggregated perturbation embeddings of all perturbed genes and selected the top 5% and bottom 5% as predicted links. In one or more example implementations, the machine learning mapping system 106 excludes self-links as the cosine similarity for these is one and biases the recall computation.

The machine learning mapping system 106 then calculates the recall as the proportion of the intersection of those predicted links with a known relationship based on sources Reactome or SIGNOR to the total number of interactions in the same source between the perturbed genes.

For cluster relationships, in one or more implementations, the machine learning mapping system 106 stratifies the above calculation by cluster for Reactome, SIGNOR, or CORUM clusters. That is, for each cluster, the machine learning mapping system 106 generates all gene pairs excluding self-links and used this set as a ground truth known gene relationships for that cluster. Then, similar to the calculation above for pairwise relationships, the machine learning mapping system 106 calculates recall at the top 5% and bottom 5% of the cosine similarity distribution of all possible pairs of perturbed genes. This type of cluster stratification allows the machine learning mapping system 106 to identify which areas of biology can and which cannot be captured using the built map.

Figure 12:
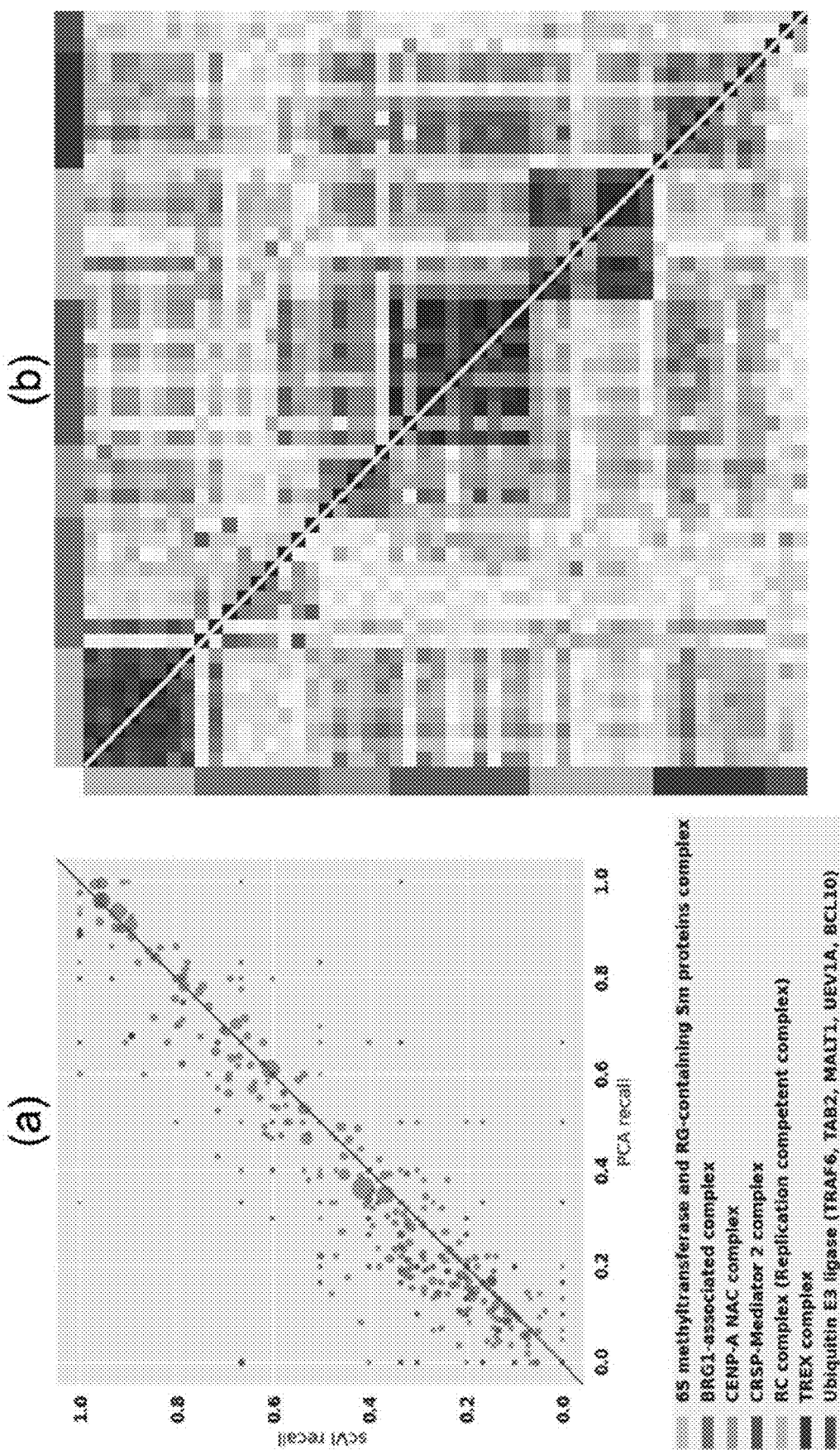
FIG. 12 illustrates a scatter plot representing recall value and a cosine similarity heatmap in accordance with one or more embodiments.

Recall results on Replogle data for different alignment and filtering choices can be found in FIG. 10, showing a slight advantage of using scVI for alignment over PCA. Known relationship counts for different comparisons in FIG. 10 can be found in FIG. 11. FIG. 12 illustrates how the two maps generated using scVI vs PCA compare in terms of the recall value per cluster in the CORUM dataset.

In one or more embodiments, the machine learning mapping system 106 can generate a split heatmap, for example, as illustrated in FIGS. 12 part (b), 16a, and 16b. As used herein, the term "split heatmap" refers to a visualization representing the strength of pairwise relationships between perturbation classes within two distinct datasets of perturbation classes. For example, these relationships are separated into two sectors, determined by the diagonal line running from the upper left to the lower right. Further, relationships along the diagonal have values representing perfect similarity (1 in this example). Moreover, relationships found above this diagonal are associated with the first dataset and relationships below the diagonal are associated with the second dataset. In one or more embodiments, labels along the rows and columns (not shown in FIG. 12 part (b)) allow users to read out pairwise similarities from either dataset in the same plot and symmetry across the diagonal highlights similarities and differences between the two datasets.

In particular, FIG. 12 part (a) illustrates a scatter plot representing the recall value for each of the CORUM protein complexes from the scVI (y-axis) vs PCA (x-axis) transcriptomic maps. Each dot represents a complex, and the size of a dot represents the number gene subunits in the associated complex. FIG. 12 part (b) illustrates a cosine similarity heatmap for genes in seven of the CORUM complexes, where the scVI map is shown below the diagonal and PCA map is shown above the diagonal (gene labels have been removed but can be found, along with colors on the axes, in High-Resolution Genome-wide Mapping of Chromosome-arm-scale Truncation Induced by CRISPR-Cas9 Editing published in bioRxiv on Apr. 15, 2023, which is incorporated by reference herein). Each color on the axes represents a different complex, as annotated in the legend. In this embodiment, the machine learning mapping system 106 looks at all genes with no transcriptoprint filtering. Clusters are more visible on the scVI side of the heatmap, as consistent with the larger sc VI recall for those clusters, as indicated by the dots with corresponding colors on the scatter plot in (a). Consistent with the summary metrics in FIG. 10, scVI performs better for most of the clusters.

Figure 13A:
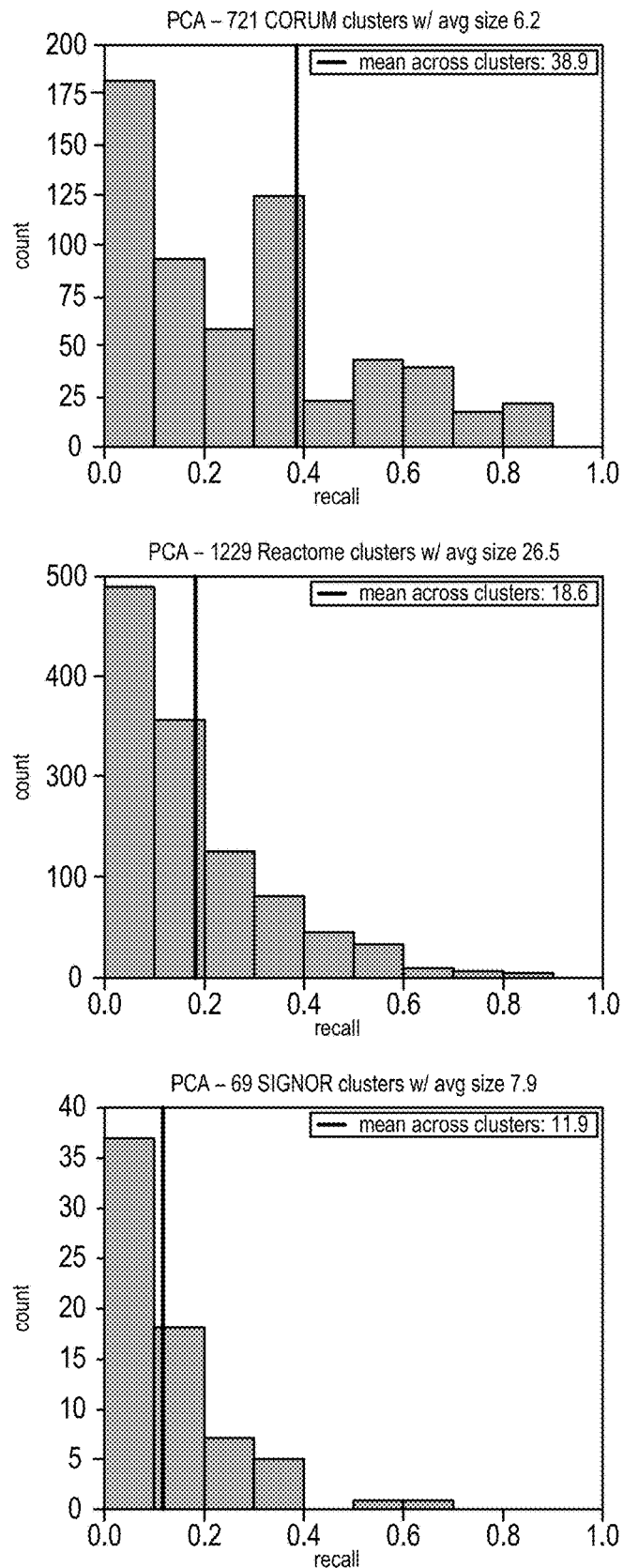
FIGS. 13A and 13B illustrate histograms representing the distribution of recall values across clusters for various benchmark sources and embedding models in accordance with one or more embodiments.
Figure 13B:
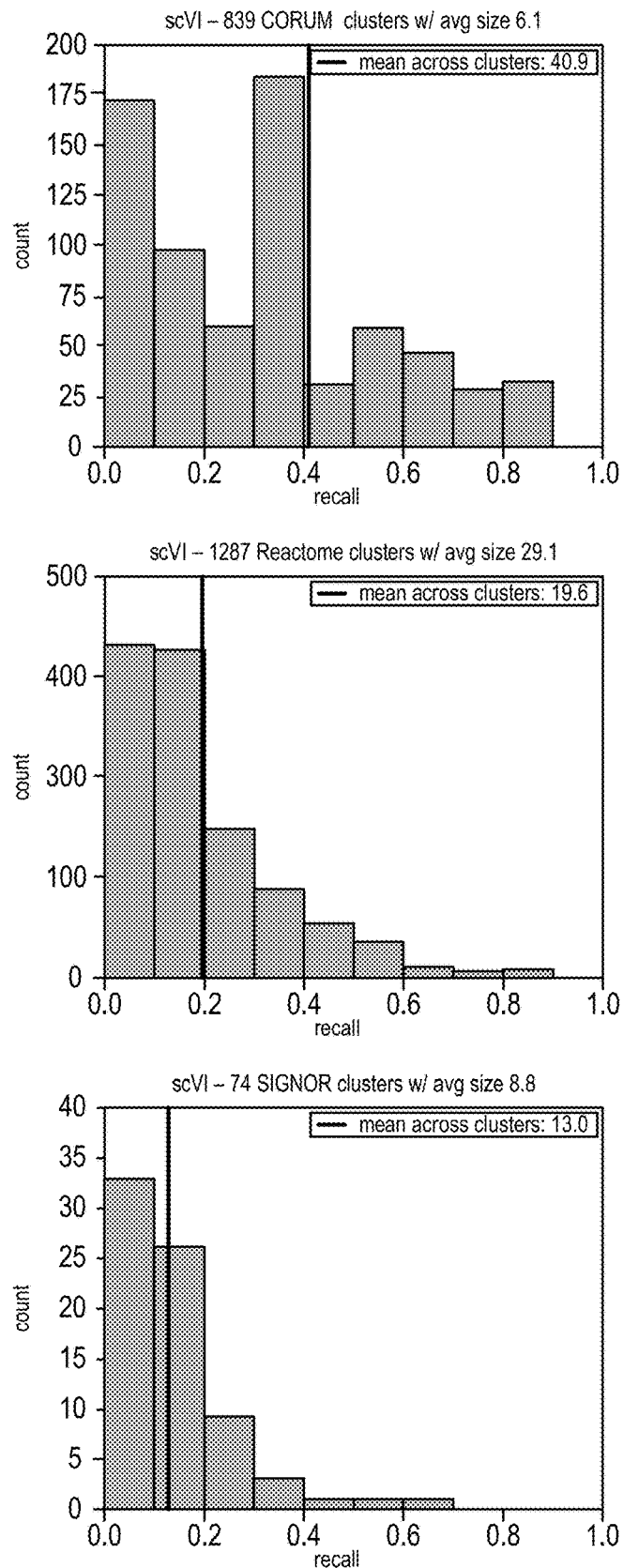

FIGS. 13A and 13B show the distribution of the recall values across clusters for different cluster sources and EFAAR choices. In particular, FIGS. 13A and 13B illustrate histograms representing the distribution of recall values across clusters for each benchmark source (rows) and embedding model (columns) when multivariate metrics are computed on Replogle data. Number of clusters and average cluster size are different for each cluster source, as indicated in the title for each plot. They are also different for PCA vs scVI for the same source since sc VI leads to more genes with transcriptoprints and the recall values shown here are computed after filtering for such genes.

For the Recursion phenomic data, researchers report recall results relative to CNN-BC (a CNN model with a batch correction component) as a baseline. As shown, an alignment step by TVN or Centerscale leads to a considerable increase in a majority of metrics compared to the baseline (see FIG. 14), and TVN typically performs better than Centerscale as it did for the univariate benchmarks in FIG. 7. Known relationship counts for different comparisons in FIG. 14 can be found in FIG. 15.

Figure 16:
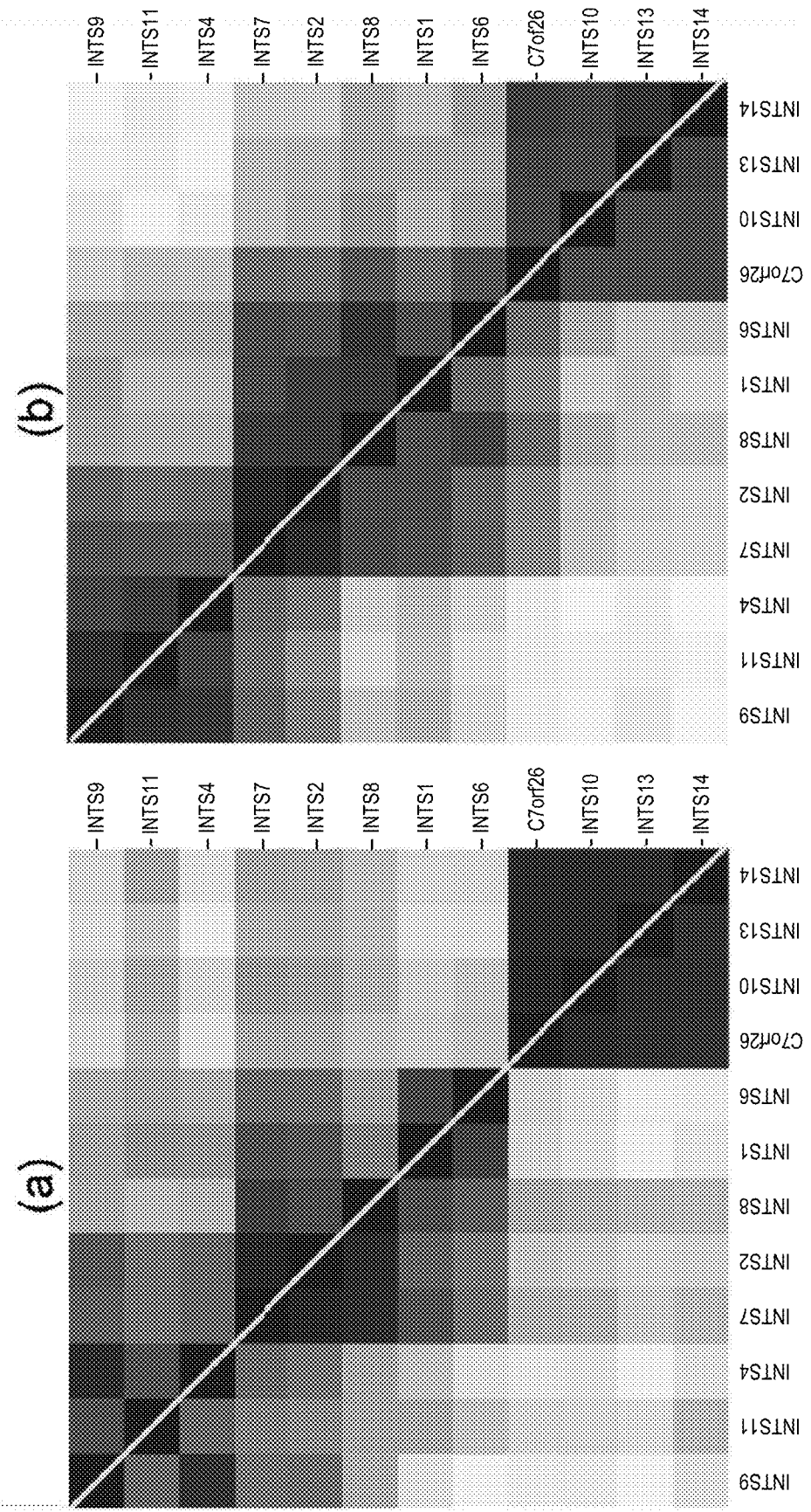
FIG. 16 illustrates cosine similarity heatmaps in accordance with one or more embodiments.

As an example of the known biology identified by the benchmarked EFAAR pipeline choices, FIG. 16 examines the cosine similarity structure for the Integrator complex which was also explored in Replogle. In particular, FIG. 16 illustrates cosine similarity heatmaps of the Integrator complex subunits from (a) the two transcriptomic maps based on Replogle data and (b) the two Recursion phenomic maps. In (a), sc VI map is shown below the diagonal and PCA map is shown above the diagonal, and in (b), TVN map is shown below the diagonal and Centerscale map is shown above the diagonal. The embodiment illustrated in FIG. 16 considers all genes with no perturbation print filtering. There are three main clusters visible in each of the four maps, which correspond to the three main modules of the integrator complex: endonuclease module including INTS4, INTS9, and INTS11 (top cluster); structural shoulder and backbone including INTS1, INTS2, INTS6, INTS7, and INTS8 (middle cluster), and enhancer module including INTS10, INTS13, and INTS14 (bottom cluster). C7 or f26, which is clustered by each of the four maps as part of the enhancer module, was officially renamed INTS15 in January 2022 after it was suggested to be a subunit of the Integrator complex. As illustrated, both of the scVI-based and PCA-based EFAAR pipelines tested on Replogle data and both of the TVN-based and Centerscale-based EFAAR pipelines on Recursion data accurately identify the modular structure of the Integrator complex.

Thus, the machine learning mapping system 106 can provide a framework for systematically constructing whole-genome maps of biology and benchmarking their performance globally with publicly available gene annotation datasets. The machine learning mapping system 106 can generate several map options, including two tested options described above built using two orthogonal data types: singlecell transcriptomic data with treatment with CRISPR interference (Perturb-Seq) and array-based phenotypic screening with CRISPR knockout. Results demonstrate the impact of different processing pipelines and metric choices. This framework can be used for a variety of large-scale biological map building applications and benchmarking efforts regardless of data types and can be expanded to include settings where additional perturbation types (small molecules, proteins, antibodies, viruses, etc.) or assay variables (growth conditions, reagent timing, etc.) are assessed.

FIGS. 1-16, the corresponding text, and the examples provide a number of different systems, methods, and non-transitory computer readable media for embedding perturbation data via a machine learning model and filtering, aligning, aggregating, and relating the embeddings to generate perturbation comparisons. In addition to the foregoing, embodiments can also be described in terms of flowcharts comprising acts for accomplishing a particular result. For example, FIG. 17 illustrates a flowchart of an example sequence of acts in accordance with one or more embodiments.

Figure 17:
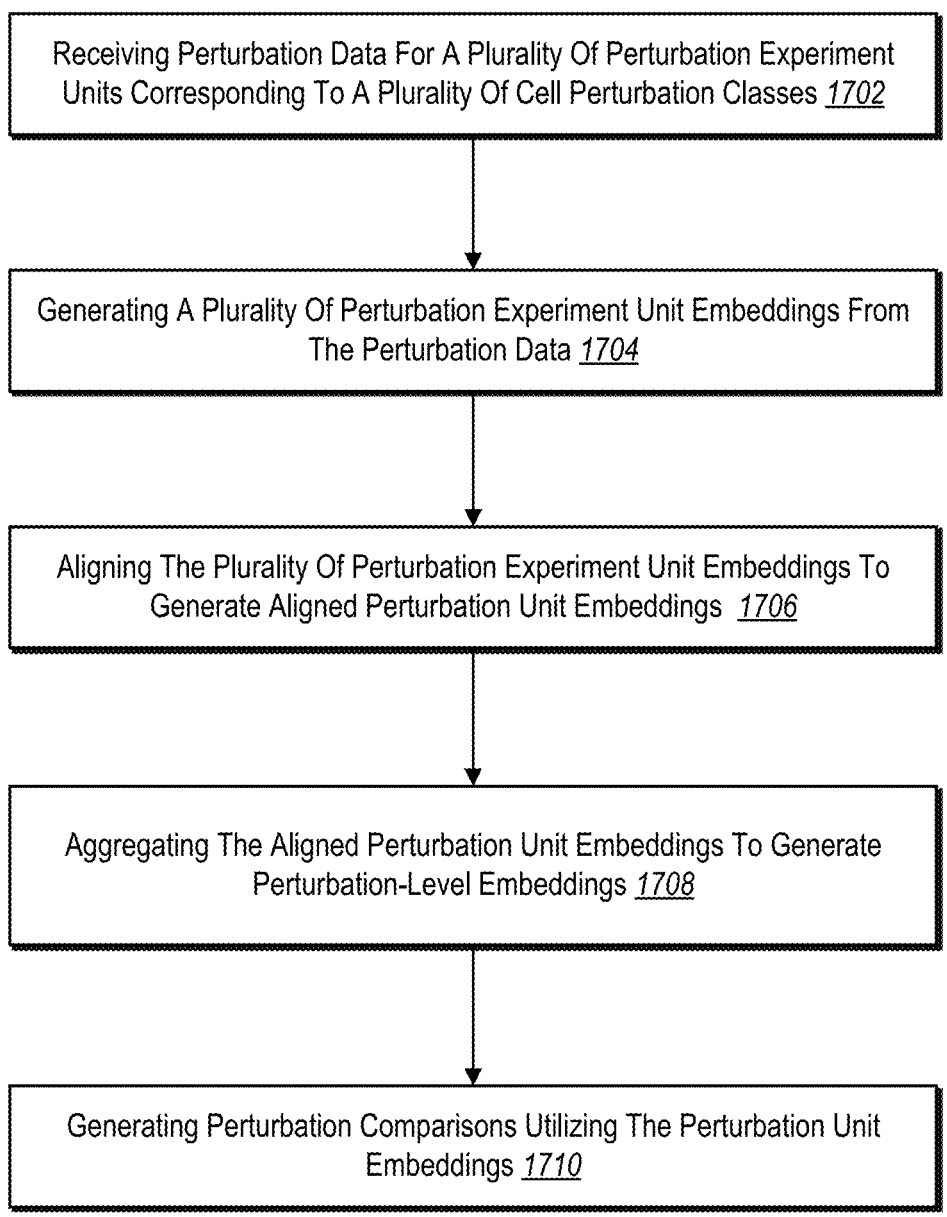
FIG. 17 illustrates an example series of acts for embedding perturbation data via a machine learning model and filtering, aligning, aggregating, and relating the embeddings to generate perturbation comparisons in accordance with one or more embodiments.

While FIG. 17 illustrates acts according to some embodiments, alternative embodiments may omit, add to, reorder, and/or modify any of the acts shown in FIG. 17. The acts of FIG. 17 can be performed as part of a method. Alternatively, a non-transitory computer readable medium can comprise instructions, that when executed by one or more processors, cause a computing device to perform the acts of FIG. 17. In still further embodiments, a system can perform the acts of FIG. 17. Additionally, the acts described herein may be repeated or performed in parallel with one another or in parallel with different instances of the same or other similar acts.

FIG. 17 illustrates an example series of acts 1700 for embedding perturbation data via a machine learning model and filtering, aligning, aggregating, and relating the embeddings to generate perturbation comparisons. The series of acts 1700 can include an act 1702 of receiving perturbation data for a plurality of perturbation experiment units corresponding to a plurality of perturbation classes; an act 1704 of generating a plurality of perturbation experiment unit embeddings from the perturbation data; an act 1706 of aligning the plurality of perturbation experiment unit embeddings to generate aligned perturbation unit embeddings; an act 1708 of aggregating the aligned perturbation unit embeddings to generate perturbation-level embeddings; and an act 1710 of generating perturbation comparisons utilizing the perturbation unit embeddings.

For example, in one or more embodiments, the series of acts 1700 can include receiving perturbation data for a plurality of perturbation experiment units corresponding to a plurality of perturbation classes; generating, utilizing a machine learning model, a plurality of perturbation experiment unit embeddings from the perturbation data; aligning, utilizing an alignment model, the plurality of perturbation experiment unit embeddings to generate aligned perturbation unit embeddings; aggregating the aligned perturbation unit embeddings to generate aggregated embeddings; and generating perturbation comparisons utilizing the perturbation-level embeddings.

In one or more implementations, aggregating the aligned perturbation unit embeddings includes aggregating the aligned perturbation unit embeddings to generate at least one of well-level embeddings, perturbation-level embeddings, gene-level embeddings, pathway-level embeddings, or mechanism of action embeddings.

Moreover, in some embodiments, generating the plurality of perturbation experiment unit embeddings from the perturbation data includes: generating, from a first transcriptomic profile of a first perturbation experiment unit, a first perturbation experiment unit embedding; and generating, from a second transcriptomic profile of a second perturbation experiment unit, a second perturbation experiment unit embedding.

In addition, in some implementations, generating the plurality of perturbation experiment unit embeddings from the perturbation data includes generating, for the plurality of perturbation experiment units, at least one of a plurality of phenomic image embeddings, a plurality of transcriptomic profile embeddings, or a plurality of invivomic embeddings.

Furthermore, in some embodiments, generating, utilizing the machine learning model, the plurality of perturbation experiment unit embeddings includes: generating, utilizing a convolutional neural network, a first perturbation experiment unit embedding for a first measurement of a first perturbation experiment unit; and generating, utilizing the convolutional neural network, a second perturbation experiment unit embedding for a second measurement of a second perturbation experiment unit.

In some implementations, the series of acts 1700 can include filtering the plurality of perturbation experiment unit embeddings according to one or more quality criterion.

Moreover, in some embodiments, aligning, utilizing the alignment model, the plurality of perturbation experiment unit embeddings to generate the aligned perturbation unit embeddings includes aligning a set of perturbation experiment unit embeddings of a single perturbation class from a plurality of different perturbation experiments according to a statistical alignment model.

In addition, in some implementations, the series of acts 1700 can include generating, utilizing a proximity bias model, proximity bias corrected perturbation experiment unit embeddings; and generating the aligned perturbation unit embeddings from the proximity bias corrected perturbation experiment unit embeddings.

Furthermore, in some embodiments, aggregating the aligned perturbation unit embeddings to generate the perturbation-level embeddings includes aggregating, utilizing an aggregation model, the aligned perturbation unit embeddings of each perturbation class to generate a perturbation-level embedding for each perturbation class.

In one or more implementations, generating the perturbation comparisons utilizing the perturbation-level embeddings includes: determining similarity measures between the perturbation-level embeddings; and providing the similarity measures for display via a client device.

FIGS. 1-16, the corresponding text, and the examples provide a number of different systems, methods, and non-transitory computer readable media for identifying perturbation data associated with a perturbation embedding model and determining a benchmark measure for the perturbation embedding model utilizing a benchmark model. In addition to the foregoing, embodiments can also be described in terms of flowcharts comprising acts for accomplishing a particular result. For example, FIG. 18 illustrates a flowchart of an example sequence of acts in accordance with one or more embodiments.

Figure 18:
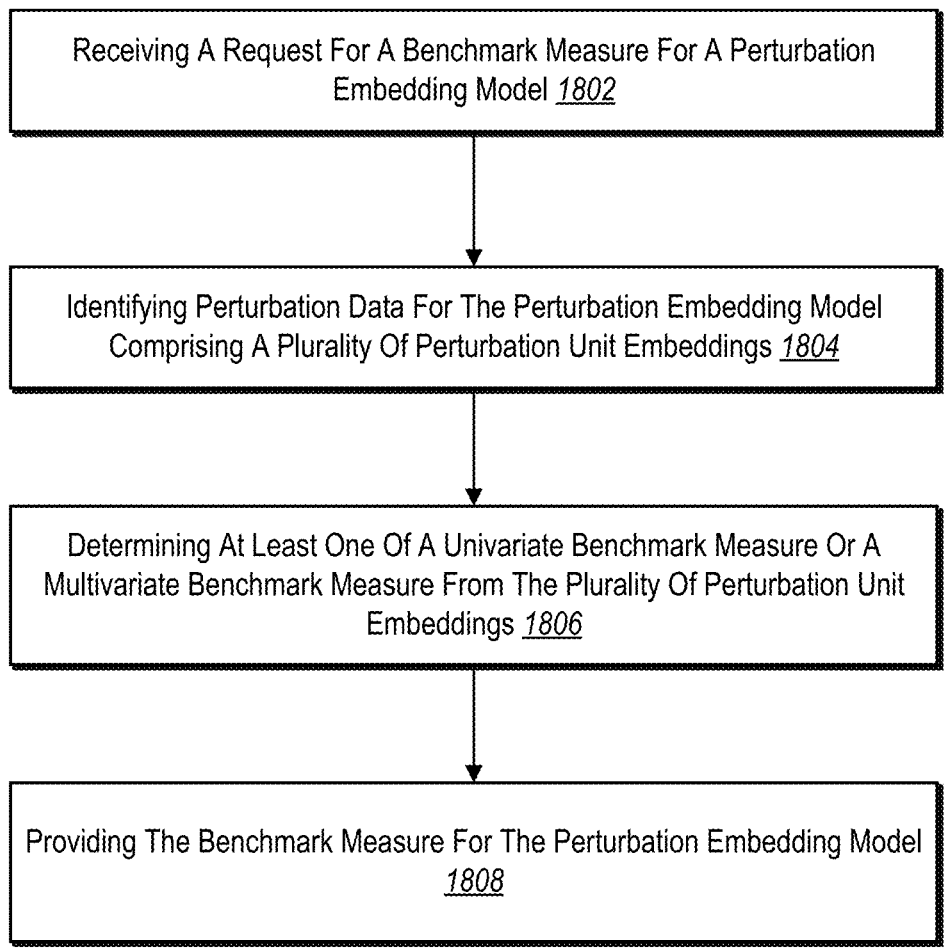
FIG. 18 illustrates an example series of acts for identifying perturbation data associated with a perturbation embedding model and determining a benchmark measure for the perturbation embedding model utilizing a benchmark model in accordance with one or more embodiments.

While FIG. 18 illustrates acts according to some embodiments, alternative embodiments may omit, add to, reorder, and/or modify any of the acts shown in FIG. 18. The acts of FIG. 18 can be performed as part of a method. Alternatively, a non-transitory computer readable medium can comprise instructions, that when executed by one or more processors, cause a computing device to perform the acts of FIG. 18. In still further embodiments, a system can perform the acts of FIG. 18. Additionally, the acts described herein may be repeated or performed in parallel with one another or in parallel with different instances of the same or other similar acts.

FIG. 18 illustrates an example series of acts 1800 for identifying perturbation data associated with a perturbation embedding model and determining a benchmark measure for the perturbation embedding model utilizing a benchmark model. The series of acts 1800 can include an act 1802 of receiving a request for a benchmark measure for a perturbation embedding model; an act 1804 of identifying perturbation data for the perturbation embedding model comprising a plurality of perturbation unit embeddings; an act 1806 of determining at least one of a univariate benchmark measure or a multivariate benchmark measure from the plurality of perturbation unit embeddings; and an act 1808 of providing the benchmark measure for the perturbation embedding model.

For example, in one or more embodiments, the series of acts 1800 can include receiving, from a client device, a request for a benchmark measure for a perturbation embedding model; identifying perturbation data for the perturbation embedding model including a plurality of perturbation unit embeddings generated by the perturbation embedding model from a plurality of perturbation experiment units corresponding to a plurality of perturbation classes; determining, utilizing a benchmark model, at least one of a univariate benchmark measure or a multivariate benchmark measure from the plurality of perturbation unit embeddings; and providing, for display via a user interface of the client device, the univariate benchmark measure or the multivariate benchmark measure for the perturbation embedding model.

In one or more implementations, the series of acts 1800 can include determining, utilizing the benchmark model, the univariate benchmark measure for the perturbation embedding model by utilizing a first perturbation unit embedding from the plurality of perturbation unit embeddings corresponding to a shared perturbation class and a second perturbation unit embedding from the plurality of perturbation unit embeddings corresponding to the shared perturbation class.

Moreover, in some embodiments, utilizing the first perturbation unit embedding and the second perturbation unit embedding includes: determining a first similarity measure between the first perturbation unit embedding and the second perturbation unit embedding; determining a second similarity measure between the first perturbation unit embedding and a third perturbation unit embedding corresponding to the shared perturbation class; determining a third similarity measure between the second perturbation unit embedding and the third perturbation unit embedding; and determining a combined similarity measure for the shared perturbation class from the first similarity measure, the second similarity measure, and the third similarity measure.

In addition, in some implementations, utilizing the first perturbation unit embedding and the second perturbation unit embedding includes at least one of: determining a cosine similarity between the first perturbation unit embedding and the second perturbation unit embedding or determining a projection similarity between the first perturbation unit embedding and the second perturbation unit embedding.

Furthermore, in some embodiments, determining, utilizing the benchmark model, the multivariate benchmark measure for the perturbation embedding model includes comparing a predicted measure of bioactivity between a first perturbation class and a second perturbation class with an observed measure of bioactivity between the first perturbation class and the second perturbation class.

In some implementations, identifying the perturbation data for the perturbation embedding model includes identifying a first perturbation-level aggregated embedding for the first perturbation class and a second perturbation-level aggregated embedding for the second perturbation class.

Moreover, in some embodiments, the series of acts 1800 can include determining the predicted measure of bioactivity between the first perturbation class and the second perturbation class by comparing the first perturbation-level aggregated embedding for the first perturbation class and the second perturbation-level aggregated embedding for the second perturbation class.

In addition, in some implementations, the series of acts 1800 can include providing, for display via the user interface of the client device, the univariate benchmark measure for the perturbation embedding model and the multivariate benchmark measure for the perturbation embedding model.

Embodiments of the present disclosure may comprise or utilize a special purpose or general-purpose computer including computer hardware, such as, for example, one or more processors and system memory, as discussed in greater detail below. Embodiments within the scope of the present disclosure also include physical and other computer-readable media for carrying or storing computer-executable instructions and/or data structures. In particular, one or more of the processes described herein may be implemented at least in part as instructions embodied in a non-transitory computer-readable medium and executable by one or more computing devices (e.g., any of the media content access devices described herein). In general, a processor (e.g., a microprocessor) receives instructions, from a non-transitory computer-readable medium, (e.g., memory), and executes those instructions, thereby performing one or more processes, including one or more of the processes described herein.

Computer-readable media can be any available media that can be accessed by a general purpose or special purpose computer system. Computer-readable media that store computer-executable instructions are non-transitory computer-readable storage media (devices). Computer-readable media that carry computer-executable instructions are transmission media. Thus, by way of example, and not limitation, embodiments of the disclosure can comprise at least two distinctly different kinds of computer-readable media: non-transitory computer-readable storage media (devices) and transmission media.

Non-transitory computer-readable storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links which can be used to carry desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures can be transferred automatically from transmission media to non-transitory computer-readable storage media (devices) (or vice versa). For example, computer-executable instructions or data structures received over a network or data link can be buffered in RAM within a network interface module (e.g., a "NIC"), and then eventually transferred to computer system RAM and/or to less volatile computer storage media (devices) at a computer system. Thus, it should be understood that non-transitory computer-readable storage media (devices) can be included in computer system components that also (or even primarily) utilize transmission media.

Computer-executable instructions comprise, for example, instructions and data which, when executed by a processor, cause a general-purpose computer, special purpose computer, or special purpose processing device to perform a certain function or group of functions. In some embodiments, computer-executable instructions are executed by a general-purpose computer to turn the general-purpose computer into a special purpose computer implementing elements of the disclosure. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the disclosure may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, and the like. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Embodiments of the present disclosure can also be implemented in cloud computing environments. As used herein, the term "cloud computing" refers to a model for enabling on-demand network access to a shared pool of configurable computing resources. For example, cloud computing can be employed in the marketplace to offer ubiquitous and convenient on-demand access to the shared pool of configurable computing resources. The shared pool of configurable computing resources can be rapidly provisioned via virtualization and released with low management effort or service provider interaction, and then scaled accordingly.

A cloud-computing model can be composed of various characteristics such as, for example, on-demand self-service, broad network access, resource pooling, rapid elasticity, measured service, and so forth. A cloud-computing model can also expose various service models, such as, for example, Software as a Service ("SaaS"), Platform as a Service ("PaaS"), and Infrastructure as a Service ("IaaS"). A cloud-computing model can also be deployed using different deployment models such as private cloud, community cloud, public cloud, hybrid cloud, and so forth. In addition, as used herein, the term "cloud-computing environment" refers to an environment in which cloud computing is employed.

Figure 19:
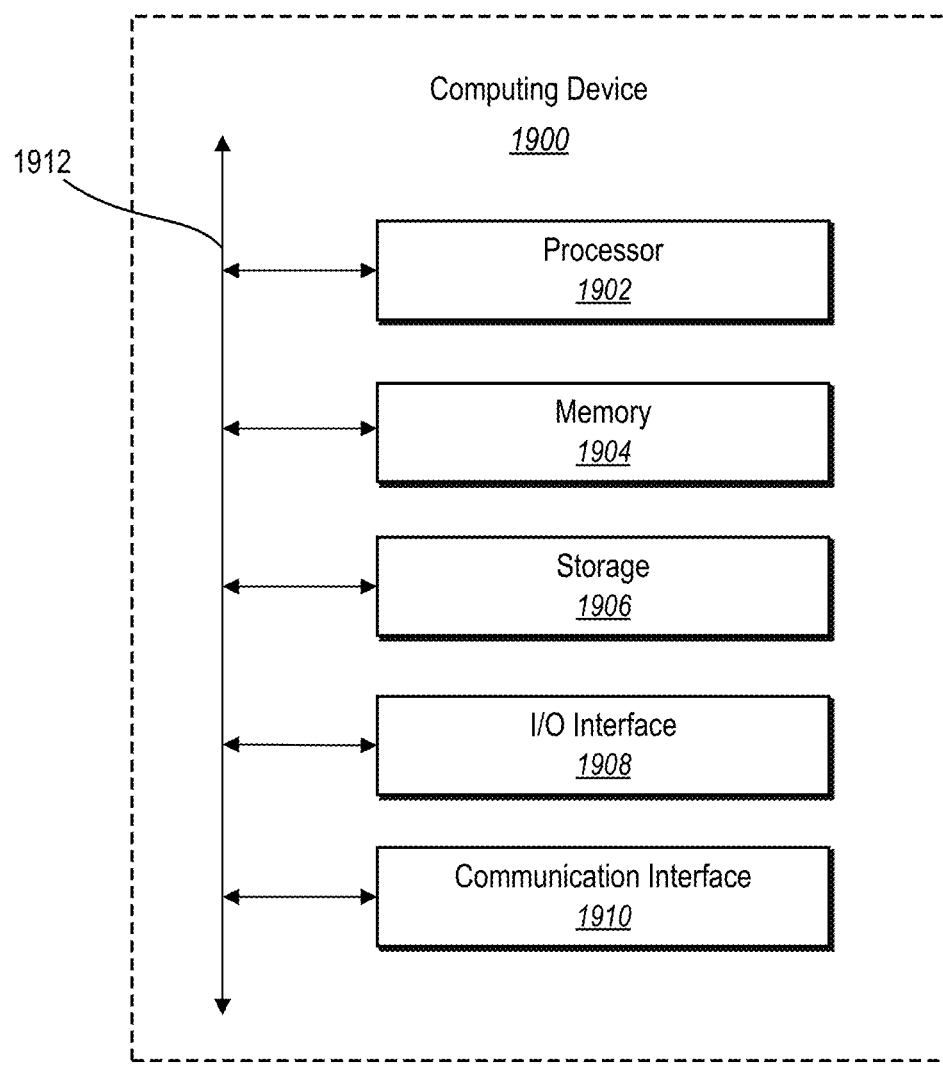
FIG. 19 illustrates a block diagram of a computing device for implementing one or more embodiments.

FIG. 19 illustrates a block diagram of an example computing device 1900 that may be configured to perform one or more of the processes described above. One will appreciate that one or more computing devices, such as the computing device 1900 may represent the computing devices described above. In one or more embodiments, the computing device 1900 may be a mobile device (e.g., a mobile telephone, a smartphone, a PDA, a tablet, a laptop, a camera, a tracker, a watch, a wearable device, etc.). In some embodiments, the computing device 1900 may be a non-mobile device (e.g., a desktop computer or another type of client device). Further, the computing device 1900 may be a server device that includes cloud-based processing and storage capabilities.

As shown in FIG. 19, the computing device 1900 can include one or more processor(s) 1902, memory 1904, a storage device 1906, input/output interfaces 1908 (or "I/O interfaces 1908"), and a communication interface 1910, which may be communicatively coupled by way of a communication infrastructure (e.g., bus 1912). While the computing device 1900 is shown in FIG. 19, the components illustrated in FIG. 19 are not intended to be limiting. Additional or alternative components may be used in other embodiments. Furthermore, in certain embodiments, the computing device 1900 includes fewer components than those shown in FIG. 19. Components of the computing device 1900 shown in FIG. 19 will now be described in additional detail.

In particular embodiments, the processor(s) 1902 includes hardware for executing instructions, such as those making up a computer program. As an example, and not by way of limitation, to execute instructions, the processor(s) 1902 may retrieve (or fetch) the instructions from an internal register, an internal cache, memory 1904, or a storage device 1906 and decode and execute them.

The computing device 1900 includes memory 1904, which is coupled to the processor(s) 1902. The memory 1904 may be used for storing data, metadata, and programs for execution by the processor(s). The memory 1904 may include one or more of volatile and non-volatile memories, such as Random-Access Memory ("RAM"), Read-Only Memory ("ROM"), a solid-state disk ("SSD"), Flash, Phase Change Memory ("PCM"), or other types of data storage. The memory 1904 may be internal or distributed memory.

The computing device 1900 includes a storage device 1906 includes storage for storing data or instructions. As an example, and not by way of limitation, the storage device 1906 can include a non-transitory storage medium described above. The storage device 1906 may include a hard disk drive (HDD), flash memory, a Universal Serial Bus (USB) drive or a combination these or other storage devices.

As shown, the computing device 1900 includes one or more I/O interfaces 1908, which are provided to allow a user to provide input to (such as user strokes), receive output from, and otherwise transfer data to and from the computing device 1900. These I/O interfaces 1908 may include a mouse, keypad or a keyboard, a touch screen, camera, optical scanner, network interface, modem, other known I/O devices or a combination of such I/O interfaces 1908. The touch screen may be activated with a stylus or a finger.

The I/O interfaces 1908 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O interfaces 1908 are configured to provide graphical data to a display for presentation to a user. The graphical data may be representative of one or more graphical user interfaces and/or any other graphical content as may serve a particular implementation.

The computing device 1900 can further include a communication interface 1910. The communication interface 1910 can include hardware, software, or both. The communication interface 1910 provides one or more interfaces for communication (such as, for example, packet-based communication) between the computing device and one or more other computing devices or one or more networks. As an example, and not by way of limitation, communication interface 1910 may include a network interface controller (NIC) or network adapter for communicating with an Ethernet or other wire-based network or a wireless NIC (WNIC) or wireless adapter for communicating with a wireless network, such as a WI-FI. The computing device 1900 can further include a bus 1912. The bus 1912 can include hardware, software, or both that connects components of computing device 1900 to each other.

In one or more implementations, various computing devices can communicate over a computer network. This disclosure contemplates any suitable network. As an example, and not by way of limitation, one or more portions of a network may include an ad hoc network, an intranet, an extranet, a virtual private network ("VPN"), a local area network ("LAN"), a wireless LAN ("WLAN"), a wide area network ("WAN"), a wireless WAN ("WWAN"), a metropolitan area network ("MAN"), a portion of the Internet, a portion of the Public Switched Telephone Network ("PSTN"), a cellular telephone network, or a combination of two or more of these.

In particular embodiments, the computing device 1900 can include a client device that includes a requester application or a web browser, such as MICROSOFT INTERNET EXPLORER, GOOGLE CHROME or MOZILLA FIREFOX, and may have one or more add-ons, plug-ins, or other extensions, such as TOOLBAR or YAHOO TOOLBAR. A user at the client device may enter a Uniform Resource Locator ("URL") or other address directing the web browser to a particular server (such as server), and the web browser may generate a Hyper Text Transfer Protocol ("HTTP") request and communicate the HTTP request to server. The server may accept the HTTP request and communicate to the client device one or more Hyper Text Markup Language ("HTML") files responsive to the HTTP request. The client device may render a webpage based on the HTML files from the server for presentation to the user. This disclosure contemplates any suitable webpage files. As an example, and not by way of limitation, webpages may render from HTML files, Extensible Hyper Text Markup Language ("XHTML") files, or Extensible Markup Language ("XML") files, according to particular needs. Such pages may also execute scripts such as, for example and without limitation, those written in JAVASCRIPT, JAVA, MICROSOFT SILVERLIGHT, combinations of markup language and scripts such as AJAX (Asynchronous JAVASCRIPT and XML), and the like. Herein, reference to a webpage encompasses one or more corresponding webpage files (which a browser may use to render the webpage) and vice versa, where appropriate.

In particular embodiments, the tech-bio exploration system 104 may include a variety of servers, sub-systems, programs, modules, logs, and data stores. In particular embodiments, the tech-bio exploration system 104 may include one or more of the following: a web server, action logger, API-request server, transaction engine, cross-institution network interface manager, notification controller, action log, third-party-content-object-exposure log, inference module, authorization/privacy server, search module, user-interface module, user-profile (e.g., provider profile or requester profile) store, connection store, third-party content store, or location store. The tech-bio exploration system 104 may also include suitable components such as network interfaces, security mechanisms, load balancers, failover servers, management-and-network-operations consoles, other suitable components, or any suitable combination thereof. In particular embodiments, the tech-bio exploration system 104 may include one or more user-profile stores for storing user profiles and/or account information for credit accounts, secured accounts, secondary accounts, and other affiliated financial networking system accounts. A user profile may include, for example, biographic information, demographic information, financial information, behavioral information, social information, or other types of descriptive information, such as interests, affinities, or location.

The web server may include a mail server or other messaging functionality for receiving and routing messages between the tech-bio exploration system 104 and one or more client devices. An action logger may be used to receive communications from a web server about a user's actions on or off the tech-bio exploration system 104. In conjunction with the action log, a third-party-content-object log may be maintained of user exposures to third-party-content objects. A notification controller may provide information regarding content objects to a client device. Information may be pushed to a client device as notifications, or information may be pulled from a client device responsive to a request received from the client device. Authorization servers may be used to enforce one or more privacy settings of the users of the tech-bio exploration system 104. A privacy setting of a user determines how particular information associated with a user can be shared. The authorization server may allow users to opt in to or opt out of having their actions logged by the tech-bio exploration system 104 or shared with other systems, such as, for example, by setting appropriate privacy settings. Third-party-content-object stores may be used to store content objects received from third parties. Location stores may be used for storing location information received from a client device associated with users.

In the foregoing specification, the invention has been described with reference to specific example embodiments thereof. Various embodiments and aspects of the invention(s) are described with reference to details discussed herein, and the accompanying drawings illustrate the various embodiments. The description above and drawings are illustrative of the invention and are not to be construed as limiting the invention. Numerous specific details are described to provide a thorough understanding of various embodiments of the present invention.

The present invention may be embodied in other specific forms without departing from its spirit or essential characteristics. The described embodiments are to be considered in all respects only as illustrative and not restrictive. For example, the methods described herein may be performed with less or more steps/acts or the steps/acts may be performed in differing orders. Additionally, the steps/acts described herein may be repeated or performed in parallel to one another or in parallel to different instances of the same or similar steps/acts. The scope of the invention is, therefore, indicated by the appended claims rather than by the foregoing description. All changes that come within the meaning and range of equivalency of the claims are to be embraced within their scope.

What is claimed is:

1. A computer-implemented method comprising:
   receiving, from a client device, a request for a benchmark measure for a perturbation embedding model;
   identifying perturbation data for the perturbation embedding model comprising a plurality of perturbation unit embeddings generated by the perturbation embedding model from a plurality of perturbation experiment units;
   determining, utilizing a benchmark model, a univariate benchmark measure from the plurality of perturbation unit embeddings by utilizing a first perturbation unit embedding from the plurality of perturbation unit embeddings corresponding to a shared perturbation class and a second perturbation unit embedding from the plurality of perturbation unit embeddings corresponding to the shared perturbation class by:
      determining a first similarity measure between the first perturbation unit embedding and the second perturbation unit embedding;
      determining a second similarity measure between the first perturbation unit embedding and a third perturbation unit embedding corresponding to the shared perturbation class;
      determining a third similarity measure between the second perturbation unit embedding and the third perturbation unit embedding; and
      determining a combined similarity measure for the shared perturbation class from the first similarity measure, the second similarity measure, and the third similarity measure; and
   providing, for display via a user interface of the client device, the univariate benchmark measure for the perturbation embedding model.

2. The computer-implemented method of claim 1, wherein
   providing the univariate benchmark measure comprises providing a consistency metric or a distance metric for the plurality of perturbation unit embeddings.

3. The computer-implemented method of claim 2, wherein providing the consistency metric comprises:
   providing a consistency of observed perturbation effects on cells or subjects within the shared perturbation class; or
   providing a signal recovery of the shared perturbation class relative to a non-perturbation control class.

4. The computer-implemented method of claim 2, wherein utilizing the first perturbation unit embedding and the second perturbation unit embedding comprises at least one of: determining a cosine similarity between the first perturbation unit embedding and the second perturbation unit embedding or determining a projection similarity between the first perturbation unit embedding and the second perturbation unit embedding.

5. The computer-implemented method of claim 1, further comprising determining, utilizing the benchmark model, a multivariate benchmark measure for the perturbation embedding model comprises comparing a predicted measure of bioactivity between a first perturbation class and a second perturbation class with an observed measure of bioactivity between the first perturbation class and the second perturbation class.

6. The computer-implemented method of claim 5, wherein identifying the perturbation data for the perturbation embedding model comprises identifying a first perturbation-level aggregated embedding for the first perturbation class and a second perturbation-level aggregated embedding for the second perturbation class.

7. The computer-implemented method of claim 6, further comprising determining the predicted measure of bioactivity between the first perturbation class and the second perturbation class by comparing the first perturbation-level aggregated embedding for the first perturbation class and the second perturbation-level aggregated embedding for the second perturbation class.

8. The computer-implemented method of claim 5, further comprising providing, for display via the user interface of the client device, the univariate benchmark measure for the perturbation embedding model and the multivariate benchmark measure for the perturbation embedding model.

9. A system comprising:
at least one processor; and
at least one non-transitory computer-readable storage medium storing instructions that, when executed by the at least one processor, cause the system to:
receive, from a client device, a request for a benchmark measure for a perturbation embedding model;
identify perturbation data for the perturbation embedding model comprising a plurality of perturbation unit embeddings generated by the perturbation embedding model from a plurality of perturbation experiment units;
determine, utilizing a benchmark model, a multivariate benchmark measure from the plurality of perturbation unit embeddings by comparing a predicted measure of bioactivity between a first perturbation class and a second perturbation class with an observed measure of bioactivity between the first perturbation class and the second perturbation class; and
provide, for display via a user interface of the client device, the multivariate benchmark measure for the perturbation embedding model.

10. The system of claim 9, further comprising instructions that, when executed by the at least one processor, cause the system to determine, utilizing the benchmark model, a univariate benchmark measure for the perturbation embedding model by comparing a first perturbation unit embedding from the plurality of perturbation unit embeddings corresponding to a shared perturbation class with a second perturbation unit embedding from the plurality of perturbation unit embeddings corresponding to the shared perturbation class.

11. The system of claim 10, wherein the instructions, when executed by the at least one processor, cause the system to compare the first perturbation unit embedding with the second perturbation unit embedding by at least one of: determining a cosine similarity between the first perturbation unit embedding and the second perturbation unit embedding or determining a projection similarity between the first perturbation unit embedding and the second perturbation unit embedding.

12. The system of claim 9, wherein the instructions, when executed by the at least one processor, cause the system to determine, utilizing the benchmark model, the multivariate benchmark measure for the perturbation embedding model by comparing a predicted measure of bioactivity between a first perturbation class and a second perturbation class with an observed measure of bioactivity between the first perturbation class and the second perturbation class.

13. The system of claim 12, wherein the instructions, when executed by the at least one processor, cause the system to identify the perturbation data for the perturbation embedding model by identifying a first perturbation-level aggregated embedding for the first perturbation class and a second perturbation-level aggregated embedding for the second perturbation class.

14. The system of claim 13, further comprising instructions that, when executed by the at least one processor, cause the system to: determine the predicted measure of bioactivity between the first perturbation class and the second perturbation class by comparing the first perturbation-level aggregated embedding for the first perturbation class and the second perturbation-level aggregated embedding for the second perturbation class.

15. The system of claim 12, further comprising instructions that, when executed by the at least one processor, cause the system to: provide, for display via the user interface of the client device, a univariate benchmark measure for the perturbation embedding model and the multivariate benchmark measure for the perturbation embedding model.

16. A non-transitory computer-readable medium storing instructions that, when executed by at least one processor, cause a computing device to:
receive, from a client device, a request for a benchmark measure for a perturbation embedding model;
identify perturbation data for the perturbation embedding model comprising a plurality of perturbation unit embeddings generated by the perturbation embedding model from a plurality of perturbation experiment units;
determine, utilizing a benchmark model, a multivariate benchmark measure from the plurality of perturbation unit embeddings by comparing a predicted measure of bioactivity between a first perturbation class and a second perturbation class with an observed measure of bioactivity between the first perturbation class and the second perturbation class; and
provide, for display via a user interface of the client device, the multivariate benchmark measure for the perturbation embedding model.

17. The non-transitory computer-readable medium of claim 16, further comprising instructions that, when executed by the at least one processor, cause the computing device to: determine, utilizing the benchmark model, a univariate benchmark measure for the perturbation embedding model by comparing a first perturbation unit embedding from the plurality of perturbation unit embeddings corresponding to a shared perturbation class with a second perturbation unit embedding from the plurality of perturbation unit embeddings corresponding to the shared perturbation class.

18. The non-transitory computer-readable medium of claim 17, wherein the instructions, when executed by the at least one processor, cause the computing device to compare the first perturbation unit embedding with the second perturbation unit embedding by:
- determining a first similarity measure between the first perturbation unit embedding and the second perturbation unit embedding;
- determining a second similarity measure between the first perturbation unit embedding and a third perturbation unit embedding corresponding to the shared perturbation class;
- determining a third similarity measure between the second perturbation unit embedding and the third perturbation unit embedding; and
- determining a combined similarity measure for the shared perturbation class from the first similarity measure, the second similarity measure, and the third similarity measure.

19. The non-transitory computer-readable medium of claim 17, wherein the instructions, when executed by the at least one processor, cause the computing device to compare the first perturbation unit embedding with the second perturbation unit embedding by at least one of: determining a cosine similarity between the first perturbation unit embedding and the second perturbation unit embedding or determining a projection similarity between the first perturbation unit embedding and the second perturbation unit embedding.

20. The non-transitory computer-readable medium of claim 16, wherein the instructions, when executed by the at least one processor, cause the computing device to determine, utilizing the benchmark model, the multivariate benchmark measure for the perturbation embedding model by comparing a predicted measure of bioactivity between a first perturbation class and a second perturbation class with an observed measure of bioactivity between the first perturbation class and the second perturbation class.

* * * * *